(12) United States Patent
Hirai et al.

(10) Patent No.: US 11,414,502 B2
(45) Date of Patent: *Aug. 16, 2022

(54) FLUOROSULFONYL GROUP OR SULFONIC ACID GROUP-CONTAINING POLYMER, ITS PRODUCTION METHOD AND ITS APPLICATION

(71) Applicant: AGC Inc., Chiyoda-ku (JP)

(72) Inventors: Takeshi Hirai, Chiyoda-ku (JP); Daisuke Jomuta, Chiyoda-ku (JP); Chikaya Tamitsuji, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 296 days.

This patent is subject to a terminal disclaimer.

(21) Appl. No.: 16/801,335

(22) Filed: Feb. 26, 2020

(65) Prior Publication Data

US 2020/0190233 A1 Jun. 18, 2020

Related U.S. Application Data

(63) Continuation of application No. PCT/JP2018/032435, filed on Aug. 31, 2018.

(30) Foreign Application Priority Data

Sep. 1, 2017 (JP) .............................. JP2017-168659
May 10, 2018 (JP) .............................. JP2018-091756
May 10, 2018 (JP) .............................. JP2018-091757

(51) Int. Cl.

| | |
|---|---|
| *C08F 14/26* | (2006.01) |
| *C08F 8/12* | (2006.01) |
| *C08L 27/22* | (2006.01) |
| *H01M 8/1004* | (2016.01) |
| *C07C 303/22* | (2006.01) |

(Continued)

(52) U.S. Cl.

CPC .......... *C08F 14/26* (2013.01); *B01D 67/0093* (2013.01); *B01D 69/02* (2013.01); *B01D 71/32* (2013.01); *B01D 71/36* (2013.01); *B01D 71/82* (2013.01); *B01J 39/20* (2013.01); *C07C 303/22* (2013.01); *C07C 309/80* (2013.01); *C07C 309/82* (2013.01); *C08F 8/12* (2013.01); *C08F 16/24* (2013.01); *C08F 16/30* (2013.01); *C08F 214/26* (2013.01); *C08F 216/1475* (2020.02); *C08J 5/225* (2013.01); *C08J 5/2237* (2013.01); *C08L 27/22* (2013.01); *C25B 1/02* (2013.01); *C25B 1/04* (2013.01); *C25B 1/46* (2013.01); *C25B 13/08* (2013.01); *H01B 1/122* (2013.01); *H01M 4/8663* (2013.01); *H01M 8/10* (2013.01); *H01M 8/1004* (2013.01); *H01M 8/1007* (2016.02); *H01M 8/1023* (2013.01); *H01M 8/1039* (2013.01); *H01M 8/188* (2013.01); *H01M 10/0565* (2013.01); *H01M 50/411* (2021.01); *B01D 69/145* (2013.01); *B01D 2325/04* (2013.01); *B01D 2325/14* (2013.01); *B01D 2325/42* (2013.01); *H01M 2008/1095* (2013.01); *H01M 2300/0082* (2013.01); *Y02E 60/10* (2013.01); *Y02E 60/36* (2013.01); *Y02E 60/50* (2013.01); *Y02P 70/50* (2015.11)

(58) Field of Classification Search

CPC .... B01D 71/32; B01D 67/0093; B01D 69/02; B01D 69/145; B01D 2325/04; B01D 2325/14; B01D 2325/42; B01D 71/36; B01D 71/82; C08F 14/26; C08F 8/12; C08F 16/24; C08F 16/30; C08F 216/1475; C08F 214/26; C07C 303/22; C07C 309/80; C07C 309/82; C08J 5/2237; C08J 5/225; C08L 27/22; C25B 1/02; C25B 1/04; C25B 1/46; C25B 13/08; H01B 1/122; H01M 8/1004; H01M 4/8663; H01M 8/1007; H01M 8/1039; H01M 8/188; H01M 8/1023; H01M 8/10; H01M 10/0565; H01M 50/411; H01M 2300/0082; H01M 2008/1095; Y02E 60/10; Y02E 60/36; Y02E 60/50; Y02P 70/50; B01J 39/20

See application file for complete search history.

(56) References Cited

U.S. PATENT DOCUMENTS 11,242,420 B2 * 2/2022 Hirai ..................... B01D 71/32

FOREIGN PATENT DOCUMENTS

| JP | 2010-018674 | * | 1/2010 |
|---|---|---|---|
| JP | 2010-108646 A | | 5/2010 |

(Continued)

OTHER PUBLICATIONS

International Search Report dated Oct. 30, 2018 in PCT/JP2018/032435 filed on Aug. 31, 2018, 2 pages.

*Primary Examiner* — Patrick D Niland
(74) *Attorney, Agent, or Firm* — Element IP, PLC

(57) ABSTRACT

A fluorosulfonyl group-containing polymer having units represented by the following formula u1, a sulfonic acid group-containing polymer having fluorosulfonyl groups in the fluorosulfonyl group-containing polymer converted into sulfonic acid groups, its production method and its applications:

Formula u1

$$\phantom{xx}\begin{array}{c}\text{---}(\text{CF}_2\text{---}\text{CF})\text{---}\\ \phantom{xxxxx}|\\ \phantom{xxxxx}\text{CF}_2\text{OCF}\end{array}\begin{array}{l}{}^{R^{F1}}\text{---}\text{SO}_2\text{F}\\ {}^{R^{F2}}\text{---}\text{SO}_2\text{F}\end{array}$$

wherein $R^{F1}$ and $R^{F2}$ are a $C_{1-3}$ perfluoroalkylene group.

29 Claims, 1 Drawing Sheet

(51) Int. Cl.

| | |
|---|---|
| *C07C 309/80* | (2006.01) |
| *C07C 309/82* | (2006.01) |
| *B01D 71/32* | (2006.01) |
| *B01D 67/00* | (2006.01) |
| *B01D 69/02* | (2006.01) |
| *C08F 16/24* | (2006.01) |
| *C08F 16/30* | (2006.01) |
| *C08F 216/14* | (2006.01) |
| *C08J 5/22* | (2006.01) |
| *C25B 1/02* | (2006.01) |
| *C25B 1/04* | (2021.01) |
| *C25B 1/46* | (2006.01) |
| *H01B 1/12* | (2006.01) |
| *H01M 4/86* | (2006.01) |
| *H01M 8/1007* | (2016.01) |
| *H01M 8/1039* | (2016.01) |
| *H01M 8/18* | (2006.01) |
| *C25B 13/08* | (2006.01) |
| *H01M 8/1023* | (2016.01) |
| *C08F 214/26* | (2006.01) |
| *H01M 8/10* | (2016.01) |
| *H01M 10/0565* | (2010.01) |
| *H01M 50/411* | (2021.01) |
| *B01D 71/36* | (2006.01) |
| *B01D 71/82* | (2006.01) |
| *B01J 39/20* | (2006.01) |
| *B01D 69/14* | (2006.01) |

(56) References Cited

FOREIGN PATENT DOCUMENTS

| | | |
|---|---|---|
| JP | 2010-284948 A | 12/2010 |
| JP | 2017-025242 A | 2/2017 |
| WO | WO 2005/003062 A2 | 1/2005 |
| WO | WO 2007/013532 A1 | 2/2007 |
| WO | WO 2007/013533 A1 | 2/2007 |

* cited by examiner

FLUOROSULFONYL GROUP OR SULFONIC ACID GROUP-CONTAINING POLYMER, ITS PRODUCTION METHOD AND ITS APPLICATION

This application is a continuation of PCT Application No. PCT/JP2018/032435, filed on Aug. 31, 2018, which is based upon and claims the benefit of priority from Japanese Patent Application No. 2017-168659 filed on Sep. 1, 2017, Japanese Patent Application No. 2018-091756 and Japanese Patent Application No. 2018-091757 filed on May 10, 2018. The contents of those applications are incorporated herein by reference in their entireties.

TECHNICAL FIELD

The present invention relates to a fluorosulfonyl group-containing polymer, a sulfonic acid group-containing polymer, its production method and its application.

BACKGROUND ART

A polymer contained in a catalyst layer or a polymer electrolyte membrane in a membrane/electrode assembly for a polymer electrolyte fuel cell, a cation exchange membrane to be used for alkali chloride electrolysis, etc. is desired to have a high ion exchange capacity. When the ion exchange capacity is high, the ion conductivity improves, and accordingly, for example, practical advantages are expected, such as an improvement of power generation performance of a polymer electrolyte fuel cell and a reduction of the electric power consumption rate by a reduction of overvoltage of a membrane resistance or the like in alkali chloride electrolysis.

As a polymer having a high ion exchange capacity, a sulfonic acid group-containing polymer formed by converting fluorosulfonyl groups in a fluorosulfonyl group-containing polymer having units based on a monomer having two fluorosulfonyl groups in one molecule and units based on tetrafluoroethylene, into sulfonic acid groups, has been proposed (Patent Documents 1 to 3).

PRIOR ART DOCUMENTS

Patent Documents

Patent Document 1: WO2005/003062
Patent Document 2: WO2007/013532
Patent Document 3: WO2007/013533

DISCLOSURE OF INVENTION

Technical Problem

However, it is necessary to increase the proportion of units based on a fluorosulfonyl group-containing monomer in a fluorosulfonyl group-containing polymer for sufficiently increasing the ion exchange capacity of the sulfonic acid group-containing polymer. The following problems thereby result.

If the proportion of the units based on a fluorosulfonyl group-containing monomer in a fluorosulfonyl group-containing polymer is increased, the glass transition temperature of the fluorosulfonyl group-containing polymer will be low, and the handling efficiency, the storage stability, etc. of the fluorosulfonyl group-containing polymer will deteriorate.

If the glass transition temperature of a fluorosulfonyl group-containing polymer becomes low, the softening temperature of a sulfonic acid group-containing polymer also becomes low. Further, if the proportion of units based on a fluorosulfonyl group-containing monomer in a fluorosulfonyl group-containing polymer is increased, the proportion of units having a sulfonic acid group in a sulfonic acid group-containing polymer increases, and the moisture content of the sulfonic acid group-containing polymer increases. As a result, the mechanical strength of a membrane comprising a sulfonic acid group-containing polymer at a high temperature deteriorates.

If the proportion of units based on a fluorosulfonyl group-containing monomer in a fluorosulfonyl group-containing polymer is increased, the fluorosulfonyl group-containing polymer and a sulfonic acid group-containing polymer become expensive, since the fluorosulfonyl group-containing monomer is expensive.

It is an object of the present invention to provide a fluorosulfonyl group-containing polymer which is excellent in the handling efficiency and the storage stability and is inexpensive as compared with conventional one, whereby a sulfonic acid group-containing polymer having a high ion exchange capacity and mechanical strength at a high temperature can be obtained, a sulfonic acid group-containing polymer, a method for producing the polymer, a liquid composition comprising the polymer, a membrane comprising the polymer, its production method, and various applications of the membrane comprising the polymer.

Solution to Problem

The present invention has the following features.
(1) A fluorosulfonyl group-containing polymer having units represented by the following formula u1:

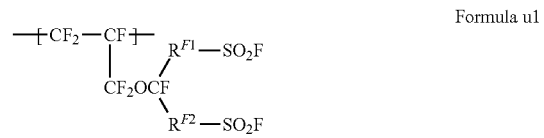

Formula u1 wherein $R^{F1}$ and $R^{F2}$ are a $C_{1-3}$ perfluoroalkylene group.
(2) The fluorosulfonyl group-containing polymer according to the above (1), which further has units based on tetrafluoroethylene.
(3) The fluorosulfonyl group-containing polymer according to the above (1) or (2), which has a volume flow rate (TQ value) of from 200 to 330° C.
(4) The fluorosulfonyl group-containing polymer according to any one of the above (1) to (3), which has a glass transition temperature (Tg) of from 5 to 70° C.
(5) A sulfonic acid group-containing polymer having units represented by the following formula u2:

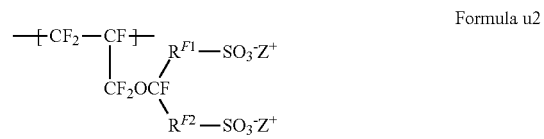

Formula u2 wherein $R^{F1}$ and $R^{F2}$ are a $C_{1-3}$ perfluoroalkylene group, and $Z^+$ is $H^+$, a metal ion or an ammonium ion.

(6) The sulfonic acid group-containing polymer according to the above (5), which further has units based on tetrafluoroethylene.

(7) The sulfonic acid group-containing polymer according to the above (5) or (6), which has an ion exchange capacity of from 0.5 to 2.5 meq/g dry resin.

(8) The sulfonic acid group-containing polymer according to any one of the above (5) to (7), which has a softening temperature of from 100 to 180° C.

(9) The sulfonic acid group-containing polymer according to any one of the above (5) to (8), which has a moisture content (mass basis) of from 30 to 300%.

(10) A method for producing a sulfonic acid group-containing polymer, which comprises hydrolyzing fluorosulfonyl groups in the fluorosulfonyl group-containing polymer as defined in any one of the above (1) to (4) into salt form sulfonic acid groups, or hydrolyzing fluorosulfonyl groups in the fluorosulfonyl group-containing polymer as defined in the above (1) or (2) into salt form sulfonic acid groups and converting the salt form sulfonic acid groups into acid form sulfonic acid groups.

(11) The method for producing a sulfonic acid group-containing polymer according to the above (10), wherein the sulfonic acid group-containing polymer after the hydrolysis or formation into an acid form is immersed in a hydrogen peroxide solution.

(12) A liquid composition which comprises the sulfonic acid group-containing polymer as defined in any one of the above (5) to (9) and a liquid medium.

(13) A membrane which comprises the sulfonic acid group-containing polymer as defined in any one of the above (5) to (9).

(14) The membrane according to the above (13), which further contains a reinforcing material.

(15) A method for producing a membrane, which comprises applying the liquid composition as defined in the above (12) on a substrate, followed by drying.

(16) A method for producing a membrane which comprises extruding the fluorosulfonyl group-containing polymer as defined in any one of the above (1) to (4) into a membrane form and converting the fluorosulfonyl groups into sulfonic acid groups.

(17) A method for producing a membrane, which comprises impregnating a reinforcing material with the liquid composition as defined in the above (12), followed by drying.

(18) A polymer electrolyte membrane which comprises the sulfonic acid group-containing polymer as defined in any one of the above (5) to (9).

(19) A catalyst layer which comprises the sulfonic acid group-containing polymer as defined in any one of the above (5) to (9) and a catalyst.

(20) A membrane/electrode assembly, wherein at least one selected from the group consisting of a catalyst later of a cathode, a catalyst layer of an anode and a polymer electrolyte membrane comprises the sulfonic acid group-containing polymer as defined in any one of the above (5) to (9).

(21) A polymer electrolyte fuel cell having the membrane/electrode assembly as defined in the above (20).

(22) A cation exchange membrane for alkali chloride electrolysis, which comprises the sulfonic acid group-containing polymer as defined in any one of the above (5) to (9).

(23) An ion exchange membrane for water electrolysis, which comprises the sulfonic acid group-containing polymer as defined in any one of the above (5) to (9).

(24) A diaphragm for a redox flow secondary cell, which comprises the sulfonic acid group-containing polymer as defined in any one of the above (1) to (9).

(25) An ion exchange membrane for an electrochemical hydrogen pump, which comprises the sulfonic acid group-containing polymer as defined in any one of the above (5) to (9).

(26) An acid form sulfonic acid group-containing fluorocarbon polymer which has a hydrogen gas permeability coefficient of at most $2.9 \times 10^{-9}$ cm$^3$·cm/(s·cm$^2$·cmHg) under conditions of a temperature of 80° C. and a relative humidity of 10%.

(27) The acid form sulfonic acid group-containing fluorocarbon polymer according to the above (26), which has an ion exchange capacity of at least 0.9 meq/g dry resin.

(28) A polymer electrolyte membrane which comprises the acid form sulfonic acid group-containing fluorocarbon polymer as defined in the above (26) or (27).

(29) The polymer electrolyte membrane according to the above (28), which has a thickness of from 5 to 200 μm.

Advantageous Effects of Invention

According to the fluorosulfonyl group-containing polymer of the present invention, a sulfonic acid group-containing polymer having a high ion exchange capacity and a high mechanical strength at a high temperature can be obtained, and it is excellent in the handling efficiency and the storage stability and is inexpensive as compared with conventional one.

The sulfonic acid group-containing polymer of the present invention has a high ion exchange capacity and a high mechanical strength at a high temperature and is inexpensive as compared with conventional one.

According to the method for producing the sulfonic acid group-containing polymer of the present invention, a sulfonic acid group-containing polymer having a high ion exchange capacity and a high mechanical strength at a high temperature and being inexpensive as compared with conventional one, can be produced.

According to the liquid composition of the present invention, a membrane comprising a polymer having a high ion exchange capacity, having a high mechanical strength at a high temperature, and being inexpensive as compared with conventional one, can be formed.

The membrane of the present invention comprises a polymer having a high ion exchange capacity, has a high mechanical strength at a high temperature and is inexpensive as compared with conventional one.

According to the method for producing a membrane of the present invention, a membrane comprising a polymer having a high ion exchange capacity, having a high mechanical strength at a high temperature, and being inexpensive as compared with conventional one, can be produced.

According to the polymer electrolyte membrane of the present invention, a membrane/electrode assembly which is excellent in the power generation performance can be obtained, and it has a high mechanical strength at a high temperature and is inexpensive as compared with conventional one.

According to the catalyst layer of the present invention, a membrane/electrode assembly which is excellent in the power generation performance can be obtained, and it has a high mechanical strength at a high temperature and is inexpensive as compared with conventional one.

The membrane/electrode assembly of the present invention is excellent in the power generation performance, a polymer electrolyte membrane or a catalyst layer has a high mechanical strength at a high temperature, and it is inexpensive as compared with conventional one.

The polymer electrolyte fuel cell of the present invention is excellent in the power generation performance, a polymer electrolyte membrane or a catalyst layer has a high mechanical strength at a high temperature, and it is inexpensive as compared with conventional one.

By the cation exchange membrane for alkali chloride electrolysis of the present invention, overvoltage of a membrane resistance or the like in alkali chloride electrolysis can be reduced, whereby the electric power consumption rate can be reduced, and it has a high mechanical strength at a high temperature and is inexpensive as compared with conventional one.

By the ion exchange membrane for water electrolysis of the present invention, overvoltage of a membrane resistance or the like in water electrolysis can be reduced, whereby the electric power consumption rate can be reduced, and it has a high mechanical strength at a high temperature and is inexpensive as compared with conventional one.

The diaphragm for a redox flow secondary cell of the present invention has a high proton permeability, a low ion transport resistance and a high mechanical strength at a high temperature and is inexpensive as compared with conventional one.

The ion exchange membrane for an electrochemical hydrogen pump of the present invention has a low electric power consumption rate for proton transport or pressurization of hydrogen, has a high mechanical strength at a high temperature and is inexpensive as compared with conventional one.

The acid form sulfonic acid group-containing fluorocarbon polymer of the present invention has a high ion exchange capacity and a low hydrogen gas permeability and is inexpensive as compared with conventional one.

The polymer electrolyte membrane comprising the acid form sulfonic acid group-containing fluorocarbon polymer of the present invention has a low ion transport resistance of the membrane and a high hydrogen gas barrier property and is inexpensive as compared with conventional one.

Figure 1:
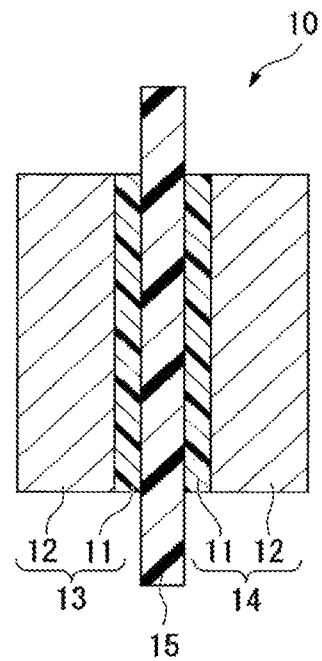
FIG. 1 is a schematic cross-sectional view showing an example of the membrane/electrode assembly of the present invention.

DESCRIPTION OF EMBODIMENTS (Definitions of Terms, Etc.)

The following definitions of terms and ways of expressions apply throughout the present specification and the scope of Claims.

A compound represented by the formula 1 is referred to as "compound 1". Compounds represented by other formulae are similarly referred.

Units represented by the formula u1 are referred to as "units u1". Structural units represented by other formulae are similarly referred.

"Units based on a monomer" is a collective term of an atomic group directly formed by polymerization of one molecule of a monomer and an atomic group obtained by chemically converting a part of the atomic group.

"Sulfonic acid group" is a collective term of a salt form sulfonic acid group ($-SO_3^-M^+$ wherein $M^+$ is a metal ion or an ammonium ion) and an acid form sulfonic acid group ($-SO_3^-H^+$).

The expression "to" showing a numerical range is used to include the numerical values before and after it as the lower limit value and the upper limit value.

(Fluorosulfonyl Group-Containing Monomer)

The fluorosulfonyl group-containing monomer of the present invention is compound 7 and used for producing the fluorosulfonyl group-containing polymer of the present invention.

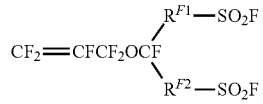

Formula 7 wherein $R^{F1}$ and $R^{F2}$ are a $C_{1-3}$ perfluoroalkylene group. $R^{F1}$ and $R^{F2}$ may be the same or different.

As $R^{F1}$ and $R^{F2}$, $-CF_2-$, $-CF_2CF_2-$, $-CF(CF_3)-$, $-CF_2CF_2CF_2-$, $-CF(CF_2CF_3)-$, $-CF(CF_3)CF_2-$, $-CF_2CF(CF_3)-$, $-C(CF_3)(CF_3)-$, etc. may be mentioned. $R^{F1}$ and $R^{F2}$ preferably have one or two carbon atoms and are preferably linear, whereby starting materials are more inexpensive, the production of the compound 7 is easy, and a sulfonic acid group-containing polymer to be produced from a fluorosulfonyl group-containing monomer has a higher ion exchange capacity. Specifically, $-CF_2-$, $-CF_2CF_2-$ or $-CF(CF_3)-$ is preferred, and $-CF_2-$ is more preferred.

The compound 7 may, for example, be compound 7-1.

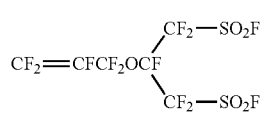

Formula 7-1

As the fluorosulfonyl group-containing compound which is useful as an intermediate for the compound 7, compound 4 or compound 5 may be mentioned. In the presence of hydrogen fluoride (HF), the compound 5 may be in an equilibrium state with an alcohol having hydrogen fluoride added to a O=C< moiety to form HO—CF< or may be an alcohol in some cases. In this specification, the compound 5 simply described may sometimes represent either one or both of the compound 5 and the alcohol form.

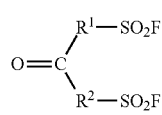

Formula 4

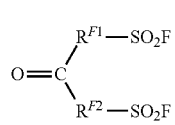

Formula 5 wherein $R^1$ and $R^2$ are a $C_{1-3}$ alkylene group. $R^1$ and $R^2$ may be the same or different.

$R^1$ and $R^2$ may, for example, be —CH$_2$—, —CH$_2$CH$_2$—, —CH(CH$_3$)—, —CH$_2$CH$_2$CH$_2$—, —CH(CH$_2$CH$_3$)—, —CH(CH$_3$)CH$_2$—, —CH$_2$CH(CH$_3$)— or —C(CH$_3$)(CH$_3$)—. $R^1$ and $R^2$ preferably have one or two carbon atoms and are preferably linear, whereby the starting material for the compound 1 is more inexpensive, the compound 5 can be easily produced, and a sulfonic acid group-containing polymer to be produced from the intermediate has a higher ion exchange capacity. Specifically, —CH$_2$—, —CH$_2$CH$_2$— or —CH(CH$_3$)— is preferred, —CH$_2$— is more preferred.

$R^{F1}$ and $R^{F2}$ are the same as $R^{F1}$ and $R^{F2}$ described for the compound 7, and preferred forms are also the same.

The compound 4 and the compound 5 can be produced as follows.

The compound 1 is reacted with a sulfonating agent to obtain compound 2, the compound 2 is reacted with a chlorinating agent to obtain compound 3, the compound 3 is reacted with a fluorinating agent to obtain compound 4, and the compound 4 is subjected to fluorination treatment to obtain compound 5.

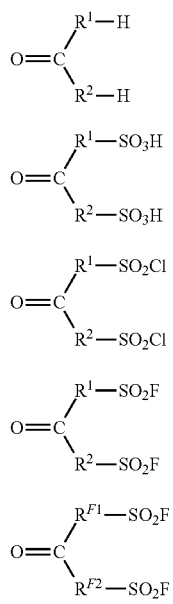

Formula 1
Formula 2
Formula 3
Formula 4
Formula 5

$R^1$ and $R^2$ are the same as $R^1$ and $R^2$ described for the compound 4, and preferred forms are also the same. $R^{F1}$ and $R^{F2}$ are the same as $R^{F1}$ and $R^{F2}$ described for the compound 7, and preferred forms are also the same.

The compound 1 may, for example, acetone, methyl ethyl ketone, diethyl ketone, methyl propyl ketone, ethyl propyl ketone, dipropyl ketone, diisopropyl ketone, isopropyl methyl ketone, isopropyl ethyl ketone or isopropyl propyl ketone. Acetone is preferred, whereby the compound 1 is more inexpensive, the compound 7 can be easily produced, and the sulfonic acid group-containing polymer has a higher ion exchange capacity per unit molecular weight.

The sulfonating agent may, for example, be chlorosulfuric acid, fluorosulfonic acid, sulfur trioxide, a complex of sulfur trioxide, fuming sulfuric acid or concentrated sulfuric acid.

The reaction temperature of the compound 1 with a sulfonating agent is preferably from 0 to 100° C. The reaction solvent may be selected from solvents which are less likely to be sulfonated themselves. The reaction solvent may, for example, be methylene chloride, chloroform, carbon tetrachloride, 1,1,1-trichloromethane, cyclohexane, hexane, petroleum ether, pentane, heptane, diethyl ether or acetonitrile. Two or more of the reaction solvents may be used in combination.

The chlorinating agent may, for example, be thionyl chloride, phosphorus pentachloride, phosphorus trichloride, phosphoryl chloride, chlorosulfuric acid, sulfuryl chloride, oxalyl chloride or chlorine.

The reaction temperature of the compound 2 with a chlorinating agent is preferably from 0 to 100° C. When the reaction temperature is at most the above upper limit value of the above range, the decomposition of the compound 3 is suppressed, whereby the yield of the compound 3 improves. When the reaction temperature is at least the lower limit value of the above range, the reaction rate increases, and the productivity thereby improves.

The fluorinating agent may, for example, be potassium hydrogen fluoride, sodium hydrogen fluoride, potassium fluoride, sodium fluoride, cesium fluoride, silver fluoride, a quaternary ammonium fluoride (such as tetraethylammonium fluoride or tetrabutylammonium fluoride), hydrogen fluoride, hydrofluoric acid or a complex of hydrogen fluoride (such as a HF-pyridine complex or HF-triethylamine).

The reaction temperature of the compound 3 with a fluorinating agent is preferably from −30 to 100° C. The reaction solvent may be selected from polar solvents and low polar solvents which are less likely to be fluorinated. The reaction solvent may, for example, be methylene chloride, chloroform, carbon tetrachloride, 1,1,1-trichloromethane, diethyl ether, dioxane, tetrahydrofuran, dimethoxyethane, diethylene glycol dimethyl ether, tetraethylene glycol dimethyl ether, dimethylsulfoxide, sulfolane, N,N-dimethylformamide, acetonitrile, dimethyl carbonate, diethyl carbonate, ethylene carbonate, propylene carbonate or water. Two or more of the reaction solvents may be used in combination.

The fluorination treatment is carried out by bringing the compound 4 into contact with fluorine gas or a fluorine compound.

The fluorine compound may, for example, be hydrogen fluoride, a halogen fluoride (such as chlorine trifluoride or iodine pentafluoride), a gaseous fluoride (such as boron trifluoride, nitrogen trifluoride, phosphorus pentafluoride, silicon tetrafluoride or sulfur hexafluoride), a metal fluoride (such as lithium fluoride or nickel(II) fluoride), a hypofluorite compound (such as trifluoromethyl hypofluorite or trifluoroacetyl hypofluorite), an electrophilic fluorination reaction agent (Selectfluor (trade name) or N-fluorobenzene sulfonimide).

The fluorination treatment is preferably treatment of bringing the compound 4 into contact with fluorine gas, whereby handling is easy, and impurities to be contained in the compound 5 can be reduced. Fluorine gas may be diluted with an inert gas such as nitrogen gas. The temperature of the fluorination treatment is preferably from −20 to 350° C. The reaction solvent may be selected from solvents in which solubility of the compound 4 or the compound 5 is high and which are less likely to be susceptible to fluorination treatment themselves. The reaction solvent may, for example, be acetonitrile, chloroform, dichloromethane, trichlorofluoromethane, a perfluorotrialkylamine (such as perfluorotributylamine), a perfluorocarbon (such as perfluorohexane or perfluorooctane), a hydrofluorocarbon (such as 1H,4H-perfluorobutane or 1H-perfluorohexane), a hydrochlorofluorocarbon (such as 3,3-dichloro-1,1,1,2,2-pentafluoropropane or 1,3-dichloro-1,1,2,2,3-pentafluoropropane) or a hydrofluoroether (such as CF$_3$CH$_2$OCF$_2$CF$_2$H).

The compound 7 is produced by reacting the compound 5 with a perfluoroallylating agent. The perfluoroallylating agent may, for example, be a compound 6.

CF$_2$=CFCF$_2$-G            Formula 6 wherein G is —OSO$_2$F, —OSO$_2$R$^{f2}$, a chlorine atom, a bromine atom or an iodine atom, and R$^{f2}$ is a C$_{1-8}$ perfluoroalkyl group.

The compound 6 is preferably compound 6-1 from the viewpoint of availability of starting materials, the reactivity of the perfluoroallylating agent, the simplicity of synthesis and the handling efficiency.

CF$_2$=CFCF$_2$OSO$_2$F            Formula 6-1

For example, the compound 6-1 may be produced by reacting hexafluoropropylene and sulfur trioxide in the presence of boron trifluoride. A Lewis acid such as a boron trifluoride diethyl ether complex or trimethoxyborane may also be used instead of boron trifluoride.

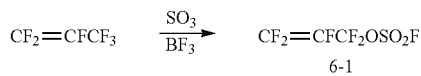

The reaction of the compound 5 with a perfluoroallylating agent is preferably carried out in the presence of a fluoride salt. The fluoride salt may, for example, be potassium fluoride, cesium fluoride, silver fluoride, quaternary ammonium fluoride or sodium fluoride.

The reaction temperature of the compound 5 with a perfluoroallylating agent is preferably from −70 to 40° C. The reaction solvent preferably contains an aprotic polar solvent and more preferably consists of an aprotic polar solvent only. The aprotic polar solvent may, for example, be monoglyme, diglyme, triglyme, tetraglyme, acetonitrile, propionitrile, adiponitrile, benzonitrile, dioxane, tetrahydrofuran, N,N-dimethylformamide, dimethylsulfoxide, N-methylpyrrolidone or nitroethane. Two or more of the reaction solvents may be used in combination.

By the above-described method for producing the compound 7, monomers having two fluorosulfonyl groups in one molecule can be produced at a low cost, since the starting materials such as the compound 1 are inexpensive, and the yield on the compound 1 basis is high. The compound 7 obtained by such a method is inexpensive as compared with conventional monomers having two fluorosulfonyl groups in one molecule.

Further, the above-described compound 4 and compound 5 are useful as intermediates for the compound 7. Further, the compound 4 and the compound 5 can be produced at a low cost by the method for producing the compound 4 and the compound 5, since starting materials such as the compound 1 are inexpensive, and the yield on the compound 1 basis is high. Further, they can be produced by a smaller number of synthetic steps.

(Fluorosulfonyl Group-Containing Polymer)

The fluorosulfonyl group-containing polymer (hereinafter referred to also as "polymer F") of the present invention has units u1. The units u1 may, for example, be units based on the compound 7.

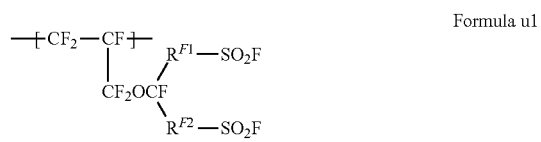

R$^{F1}$ and R$^{F2}$ are the same as R$^{F1}$ and R$^{F2}$ described for the compound 7, and preferred forms are also the same.

The polymer F preferably has units based on tetrafluoroethylene (hereinafter referred to also as "TFE"). TFE has an effect to improve crystallinity of a polymer, whereby the after-described swelling is suppressed when the sulfonic acid group-containing polymer absorbs water, and the moisture content of the sulfonic acid group-containing polymer can be reduced. By reducing the moisture content, a polymer electrolyte membrane to be formed has a high mechanical strength. Further, when used in a catalyst layer, flooding of a polymer electrolyte fuel cell can be suppressed.

The polymer F may further have units based on a monomer other than the compound 7 and TFE.

Such other monomer may, for example, be chlorotrifluoroethylene, trifluoroethylene, vinylidene fluoride, vinyl fluoride, ethylene, propylene, perfluoro(3-butenyl vinyl ether), a perfluoro(allyl vinyl ether), a perfluoro α-olefin (such as hexafluoropropylene), a (perfluoroalkyl)ethylene (such as (perfluorobutyl)ethylene), a (perfluoroalkyl)propene (such as 3-perfluorooctyl-1-propene), a perfluoro(alkyl vinyl ether) or a perfluoromonomer having a 5-membered ring described in WO2011/013578.

In all units constituting the polymer F, the proportion of units u1, units based on TFE and units based on other monomer may be appropriately determined depending on characteristics and physical properties required for the sulfonic acid group-containing polymer, or the after-described liquid composition (such as ion exchange capacity, volume flow rate (TQ value), glass transition temperature (Tg), moisture content, ion conductivity, mechanical strength, elastic modulus, softening temperature, free volume, gas permeability, hydrogen gas permeability, water vapor permeability, diffusibility of water, transport number, degree of swelling, size of phase separation structure, dispersible particle size in the liquid composition, viscosity of the liquid composition or storage elastic modulus of the liquid composition).

The volume flow rate (TQ value) of the polymer F is preferably from 200 to 330° C., more preferably from 205 to 260° C. When the TQ value is at least the lower limit value of the above range, the sulfonic acid group-containing polymer has a sufficient molecular weight and is excellent in the mechanical strength. When the TO value is at most the upper limit value of the above range, the sulfonic acid group-containing polymer has good solubility or dispersibility, and the after-mentioned liquid composition can be easily prepared. The TQ value is an index of the molecular weight of the polymer F.

The glass transition temperature (Tg) of the polymer F is preferably from 5 to 70° C., more preferably from 15 to 55° C. When Tg is at least the lower limit value of the above range, the tack property of the polymer F is suppressed, and the handling efficiency and the storage stability will be good. When Tg is at most the upper limit value of the above range, fragility of pellets or a membrane of the polymer F is suppressed.

The polymer F can be produced by polymerizing a monomer component containing the compound 7 and as the case requires, TFE and other monomer.

As the polymerization method, a bulk polymerization method, a solution polymerization method, a suspension polymerization method, an emulsion polymerization method, etc. may be mentioned. Further, the polymerization may be carried out in liquid or supercritical carbon dioxide.

The polymerization is carried out under conditions where radicals are formed. The method for forming radicals may, for example, be a method of applying radioactive rays such as ultraviolet rays, γ rays or electron rays or a method of adding a radical initiator. The polymerization temperature is preferably from 10 to 150° C.

The radical initiator may, for example, be bis(fluoroacyl) peroxide, bis(perfluoroalkyl)peroxide, bis(chlorofluoroacyl) peroxide, dialkyl peroxydicarbonate, dialkyl peroxide, peroxyester, an azo compound or a persulfate. A perfluorocompound such as bis(fluoroacyl)peroxide or bis (perfluoroalkyl)peroxide is preferred, whereby a polymer F which has a few unstable terminal group is obtained.

The solvent used in the solution polymerization method is preferably a solvent having a boiling point of from 20 to 350° C., more preferably a solvent having a boiling point of from 40 to 150° C. The solvent may, for example, be a perfluorotrialkylamine (such as perfluorotributylamine), a perfluorocarbon (such as perfluorohexane or perfluorooctane), a hydrofluorocarbon (such as 1H, 4H-perfluorobutane or 1H-perfluorohexane), a hydrochlorofluorocarbon (such as 3,3-dichloro-1,1,1,2,2-pentafluoropropane or 1,3-dichloro-1,1,2,2,3-pentafluoropropane) or a hydrofluoroether (such as $CF_3CH_2OCF_2CF_2H$).

In the solution polymerization method, monomers, a radical initiator, etc. are added in a solvent, and radicals are formed in the solvent to polymerize the monomers. The monomers and the radical initiator may be added all at once, may be sequentially added or may be continuously added.

In the suspension polymerization method, it is preferred that water is used as a dispersion medium, monomers, a nonionic radical initiator, etc. are added in the dispersion medium to form radicals in the dispersion medium to polymerize the monomers.

The nonionic radical initiator may, for example, be a bis(fluoroacyl)peroxide, a bis(chlorofluoroacyl)peroxide, a dialkyl peroxydicarbonate, a diacyl peroxide, a peroxyester, a dialkyl peroxide, a bis(fluoroalkyl)peroxide or an azo compound.

An organic solvent as an assistant, a surfactant as a dispersion stabilizer to prevent aggregation of suspended particles or a hydrocarbon compound (such as hexane or methanol) as a molecular weight modifier may, for example, be added in the dispersion medium.

In the emulsion polymerization method, monomers are emulsified in water in the presence of an emulsifier and a polymerization initiator, and the monomers are polymerized. As the emulsifier and the polymerization initiator, those usually used for emulsion polymerization of a perfluoropolymer may be used. For example, as the emulsifier, an ammonium perfluorocarboxylate such as $CF_3CF_2CF_2CF_2OCF_2COONH_4$ or $CF_3CF_2OCF_2CF_2OCF_2COONH_4$ may be used. As the polymerization initiator, a radical initiator such as a peroxide, an azo compound or a persulfate may be used. Further, the initiator may be activated by an oxidation-reduction reaction with metal ions. Further, in addition, a buffer, a chain transfer agent, etc. used in a usual emulsion polymerization of a perfluoropolymer may be appropriately used.

Further, a mixed liquid of an aqueous solvent and a fluorinated monomer may be forcibly emulsified by means of a homogenizer, a pressure emulsifier or the like before initiation of the polymerization in order to increase the reactivity of the fluorinated monomer.

The above-described polymer F has units u1 having two fluorosulfonyl groups in one molecule, whereby a sulfonic acid group-containing polymer having a high ion exchange capacity can be obtained.

Further, the units u1 have a relatively small molecular weight and two fluorosulfonyl groups, whereby even if the proportion of units based on the fluorosulfonyl group-containing monomer in the polymer F is reduced as compared with conventional polymers having units having two fluorosulfonyl groups, a sulfonic acid group-containing polymer having the ion exchange capacity at the same level can be obtained. Accordingly, the polymer F has a high Tg, and the handling efficiency and the storage stability of the polymer F will improve. The sulfonic acid group-containing polymer has a high softening temperature for the same reason. Further, the sulfonic acid group-containing polymer has a low moisture content per ion exchange capacity, whereby a sulfonic acid group-containing polymer which maintains the mechanical strength to a high temperature can be obtained.

Further, the polymer F has units u1 based on the inexpensive compound 7 and is thereby inexpensive as compared with conventional polymers having units based on a compound having two fluorosulfonyl groups in one molecule.

(Sulfonic Acid Group-Containing Polymer)

The sulfonic acid group-containing polymer (hereinafter referred to also as "polymer H") of the present invention has units u2.

For example, the polymer H is a polymer formed by converting fluorosulfonyl groups in the polymer F into sulfonic acid groups. In such a case, the units u2 are units derived from the units u1.

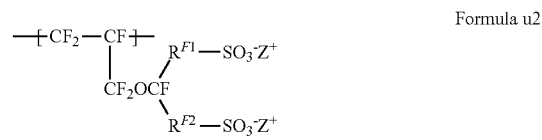

Formula u2 wherein $Z^+$ is $H^+$, a metal ion or an ammonium ion. The metal ion is preferably an alkali metal.

$R^{F1}$ and $R^{F2}$ are the same as $R^{F1}$ and $R^{F2}$ described for the compound 7, and preferred forms are also the same.

The polymer H preferably further has units based on TFE. The polymer H may further have units based on a monomer other than the compound 7 and TFE.

The polymer H preferably has an ion exchange capacity of from 0.5 to 2.5 meq/g dry resin (hereinafter the unit "meq/g dry resin" may be omitted in some cases), more preferably from 1.3 to 2.3. When the ion exchange capacity is at least the lower limit value of the above range, the polymer H has a high ion conductivity, whereby when used in a polymer electrolyte membrane or a catalyst layer for a polymer electrolyte fuel cell, sufficient power output can be obtained. Further, when used in an ion exchange membrane for alkali chloride electrolysis or water electrolysis, over-voltage of a membrane resistance or the like is lowered. When the ion exchange capacity is at most the upper limit value of the above range, swelling is suppressed when the polymer H absorbs water, whereby a polymer electrolyte membrane to be formed has a high mechanical strength. Further, when used in a catalyst layer, flooding of a polymer electrolyte fuel cell is suppressed.

The polymer H has a softening temperature of preferably from 100 to 180° C., more preferably from 120 to 170° C., further preferably from 140 to 160° C. When the softening temperature is at least the lower limit value of the above range, a polymer electrolyte membrane to be formed has a high mechanical strength at a high temperature. When the softening temperature is at most the upper limit value of the above range, the temperature for annealing treatment of a polymer electrolyte membrane or thermal press required for transferring a catalyst layer or forming a membrane/electrode assembly is made to be low.

The polymer H has a moisture content (mass basis) of preferably from 30 to 300%, more preferably from 40 to 200%. When the moisture content is at least the lower limit value of the above range, the polymer H has a high ion conductivity, whereby a membrane/electrode assembly which is further excellent in power generation performance can be obtained. When the moisture content is at most the upper limit value of the above range, the polymer H will not extensively swell by water, whereby the mechanical strength of a polymer electrolyte membrane can be maintained.

The polymer H may, for example, be obtained by converting fluorosulfonyl groups in the polymer F into sulfonic acid groups.

As a method of converting fluorosulfonyl groups into sulfonic acid groups, a method may be mentioned that fluorosulfonyl groups in the polymer F are hydrolyzed into salt form sulfonic acid groups, and the salt form sulfonic acid groups are converted into acid form so as to be acid form sulfonic acid groups. In a case where the salt form sulfonic acid groups are desired, conversion into acid form is not carried out.

The hydrolysis is carried out, for example, by bringing the polymer F into contact with a basic compound in a solvent. The basic compound may, for example, be sodium hydroxide, potassium hydroxide or triethylamine. The solvent may, for example, be water or a mixed solvent of water and a polar solvent. The polar solvent may, for example, be an alcohol (such as methanol or ethanol) or dimethylsulfoxide.

Conversion into acid form may, for example, be carried out by bringing the polymer H having salt form sulfonic acid groups into contact with an aqueous solution of e.g. hydrochloric acid, sulfuric acid or nitric acid. The temperature in the hydrolysis and conversion into acid form is preferably from 0 to 120° C. After the hydrolysis or conversion into acid form, the polymer H is preferably washed with water.

In order to remove organic substances contained as impurities in the polymer H, the polymer H may be subjected to treatment of e.g. immersing in a hydrogen peroxide solution to decompose the organic substances after the hydrolysis in the salt form sulfonic acid groups as they are or conversion into acid form.

The concentration of hydrogen peroxide in the hydrogen peroxide solution is preferably from 0.1 to 30 mass %, more preferably at least 1 mass % and less than 10 mass %. When the concentration is at least the lower limit value of the above range, the effect to decompose organic substances is sufficient. When the concentration is at most the upper limit value of the above range, the polymer H is less likely to be decomposed.

The temperature of the hydrogen peroxide solution is preferably from 15 to 90° C., more preferably at least 40° C. and less than 80° C. When the temperature is at least the lower limit value of the above range, the effect to decompose organic substances is sufficient. When the temperature is at most the upper limit value of the above range, hydrogen peroxide is less likely to be decomposed.

Time for immersing the polymer H in the hydrogen peroxide solution is, for example, preferably from 0.5 to 100 hours in a case where the polymer H has a thickness of 50 μm, although it depends on the thickness of the polymer H and the amount of organic substances contained. If the time for immersing is less than 0.5 hour, organic substances in the inside of a membrane are hardly decomposed. If the polymer H is immersed over 100 hours, the effect to further decompose organic substances is not expected.

The polymer H is preferably washed with water after immersed in the hydrogen peroxide solution. Water to be used for washing is preferably ultrapure water. Further, before washing with water, treatment for conversion into acid form may be carried out.

The sulfonic acid groups in the polymer H finally obtained after the above treatment may be either salt form or acid form. Further, the polymer H may be in a powder form, a pellet form or a membrane form.

As applications of the polymer H, a polymer contained in a liquid composition for forming a membrane containing a polymer, a polymer contained in a catalyst layer or a polymer electrolyte membrane for a membrane/electrode assembly for a polymer electrolyte fuel cell, a polymer contained in a catalyst layer or a polymer electrolyte membrane in a membrane/electrode assembly for a polymer electrolyte type water electrolysis, a polymer contained in a cation exchange membrane to be used for alkali chloride electrolysis or electrodialysis, a polymer contained in a diaphragm for a redox flow secondary cell, a polymer contained in an ion exchange membrane to be used for alkali water electrolysis or polymer electrolyte type water electrolysis, a polymer contained in an ion exchange membrane for an electrochemical hydrogen pump, a polymer contained in a cation exchange resin to be used in an ion conductive polymer actuator or a gas sensor, a polymer to be used for a solid acid catalyst, a polymer to be used for a film type humidity controlling apparatus such as a dehumidifier or a humidifier, a polymer to be used in a gas barrier membrane, etc. may be mentioned.

The above described polymer H has units u2 having two sulfonic acid groups in one molecule and thereby has a high ion exchange capacity.

Further, the units u2 have a relatively small molecular weight and two sulfonic acid groups, whereby even if the proportion of units having sulfonic acid groups in the polymer H is reduced as compared with conventional polymers having units having two sulfonic acid groups, the polymer H has an ion exchange capacity at the same level. Accordingly, the polymer H has a high softening temperature. Further, the polymer H has a low moisture content per ion exchange capacity, whereby the polymer H which maintains the mechanical strength to a high temperature can be obtained.

Further, the polymer H has units u2 derived from units u1 based on the inexpensive compound 7, whereby the polymer H is inexpensive as compared with conventional polymers having units having two sulfonic acid groups.

(Liquid Composition)

The liquid composition of the present invention comprises the polymer H and a liquid medium.

The liquid composition may be one having the polymer H dispersed in a liquid medium or one having the polymer H dissolved in a liquid medium.

The liquid medium may be water alone, an organic solvent alone or one containing water and an organic solvent, and is preferably one containing water and an organic solvent.

Water improves the dispersibility or solubility of the polymer H in the liquid medium.

A catalyst layer and a polymer electrolyte membrane which are not fragile can be easily formed with the organic solvent.

The organic solvent is preferably at least one $C_{1-4}$ alcohol with a view to easily forming a catalyst layer and a polymer electrolyte member which are not fragile.

The $C_{1-4}$ alcohol may, for example, be methanol, ethanol, 1-propanol, 2-propanol, 1-butanol, 2,2,2-trifluoroethanol, 2,2,3,3,3-pentafluoro-1-propanol, 2,2,3,3-tetrafluoro-1-propanol, 1,1,1,3,3,3-hexafluoro-2-propanol or 3,3,3-trifluoro-1-propanol.

The proportion of water is preferably from 10 to 99 mass %, more preferably from 20 to 99 mass % to the sum of water and the organic solvent.

The proportion of the organic solvent is preferably from 1 to 90 mass %, more preferably from 1 to 80 mass % to the sum of water and the organic solvent.

When the proportions of water and the organic solvent fall within the above ranges, the polymer H has excellent dispersibility in a dispersion medium, and a catalyst layer and a polymer electrolyte membrane which are not fragile can be easily formed.

The concentration of the polymer H in the liquid composition is preferably from 1 to 50 mass %, more preferably from 3 to 30 mass %. When the concentration of the polymer H is at least the lower limit value of the above range, a thick membrane can be stably obtained when forming a membrane. Further, the composition of a coating liquid for forming a catalyst layer can be easily adjusted when producing a catalyst layer. When the concentration of the polymer H is at most the upper limit value of the above range, it can be suppressed that the liquid composition has an excessively high viscosity.

The liquid composition may have at least one metal, metal compound or metal ion selected from the group consisting of cerium and manganese in order to further improve the durability of a polymer electrolyte membrane and a catalyst layer to be produced from the liquid composition.

The liquid composition is obtained by mixing the polymer H and the liquid medium.

The mixing method may, for example, be a method of applying shearing force such as stirring to the polymer H in the liquid medium under atmospheric pressure or under a sealed state by an autoclave or the like.

The temperature at the time of stirring is preferably from 0 to 250° C., more preferably from 20 to 150° C. As the case requires, shearing force such as ultrasonic wave may be applied.

When applying shearing force such as stirring to a mixed liquid of the polymer H and the liquid medium, shearing force such as stirring may be applied to a mixed liquid in which the liquid medium is added all at once to the polymer H, or the liquid medium is dividedly mixed with the polymer H plural times, and shearing force such as stirring may be applied during intervals. For example, shearing force such as stirring is applied to a mixed liquid in which a part of the liquid medium is added to the polymer H and the rest of the liquid medium is added to the mixed liquid, and shearing force such as stirring is applied again. Otherwise, only an organic solvent is added to the liquid medium and shearing force such as stirring is applied, and then only water is added, and shearing force such as stirring is applied again.

The liquid composition of the present invention has a high ion exchange capacity and a high mechanical strength at a high temperature and contains the polymer H which is inexpensive as compared with conventional one, whereby a membrane containing a polymer having a high ion exchange capacity and having a high mechanical strength at a high temperature can be formed, which is in expensive as compared with conventional one.

(Membrane)

The membrane of the present invention contains the polymer H and may further contain a reinforcing material. The membrane of the present invention may further contain components other than the polymer H and the reinforcing material.

The reinforcing material may, for example, be a porous body, fibers, a woven fabric or a non-woven fabric. As the material of the reinforcing material, various polymers may be mentioned and may be appropriately selected depending on applications of the membrane. In a case where the membrane is a polymer electrolyte membrane in a membrane/electrode assembly for a polymer electrolyte fuel cell, the material of the reinforcing material may, for example, be a polytetrafluoroethylene, a tetrafluoroethylene/hexafluoropropylene copolymer, a tetrafluoroethylene/perfluoro(alkyl vinyl ether) copolymer, a polyethylene, a polypropylene or a polyphenylene sulfide.

The method for producing the membrane of the present invention may, for example, be a method (cast method) of applying the liquid composition of the present invention on a substrate, followed by drying, or a method of extruding the polymer F into a membrane form and converting fluorosulfonyl groups into sulfonic acid groups. In a case where the reinforcing material is further contained, a method of impregnating the reinforcing material with the liquid composition of the present invention, followed by drying, or a method of impregnating the reinforcing material with a molten polymer F, and then converting the fluorosulfonyl groups into sulfonic acid groups, may be mentioned.

In a case where the membrane is a polymer electrolyte membrane in a membrane/electrode assembly for a polymer electrolyte fuel cell, the polymer electrolyte membrane may, for example, be formed by a method of applying the liquid composition on a substrate film or a catalyst layer, followed by drying.

In a case where the membrane is a catalyst layer in a membrane/electrode assembly for a polymer electrolyte fuel cell, the catalyst layer may be formed by a method of applying a catalyst layer-forming coating liquid on a polymer electrolyte membrane, a gas diffusion layer or the like, followed by drying or a method of applying a catalyst layer-forming coating liquid on a substrate film, followed by drying to form a catalyst layer and transferring the catalyst layer on a polymer electrolyte membrane. The catalyst layer-forming coating liquid may, for example, be prepared by mixing the liquid composition of the present invention and a dispersion of a catalyst.

The application of the membrane of the present invention may, for example, be a catalyst layer or a polymer electrolyte membrane in a membrane/electrode assembly for a polymer electrolyte fuel cell, a catalyst layer or a polymer electrolyte membrane in a membrane/electrode assembly for a polymer electrolyte type water electrolysis, a cation exchange membrane to be used for alkali chloride electrolysis or electrodialysis, an ion exchange membrane to be used for water electrolysis, a diaphragm for a redox flow secondary cell or an ion exchange membrane for an electrochemical hydrogen pump.

As described above, the membrane of the present invention has a high ion exchange capacity and a high mechanical strength at a high temperature, and contains the polymer H which is inexpensive as compared with conventional one and thereby contains a polymer having a high ion exchange capacity, has a high mechanical strength at a high temperature and is inexpensive as compared with conventional one.

(Membrane/Electrode Assembly)

FIG. 1 is a cross-sectional view showing an example of the membrane/electrode assembly of the present invention. The membrane/electrode assembly 10 has an anode 13 having a catalyst layer 11 and a gas diffusion layer 12, a cathode 14 having a catalyst layer 11 and a gas diffusion layer 12 and a polymer electrolyte membrane 15 arranged so as to be in contact with the catalyst layers 11 between the anode 13 and the cathode 14.

In the membrane/electrode assembly 10, at least one selected from the group consisting of the catalyst layer 11 in the cathode 14, the catalyst layer 11 in the anode 13 and the polymer electrolyte membrane 15, comprises the polymer H. In a case where the catalyst layer 11 comprises the polymer H, it is preferred that at least the catalyst layer 11 in the cathode 14 comprises the polymer H.

The catalyst layer is a layer comprising a catalyst and a polymer having an ion exchange groups.

The catalyst may, for example, be a supported catalyst having platinum or a platinum alloy supported on a carbon carrier.

The carbon carrier may, for example, be a carbon black powder.

The polymer having an ion exchange group may, for example, be the polymer H or a perfluoropolymer having an ion exchange group other than the polymer H. The ion exchange group in the polymer contained in the catalyst layer is preferably acid form, and preferably an acid form sulfonic acid group.

The gas diffusion layer has a function of uniformly diffusing gas in the catalyst layer and a function as a current collector. The gas diffusion layer may, for example, be a carbon paper, a carbon cloth or a carbon felt. The gas diffusion layer is preferably subjected to water repellent treatment with a polytetrafluoroethylene or the like.

Figure 2:
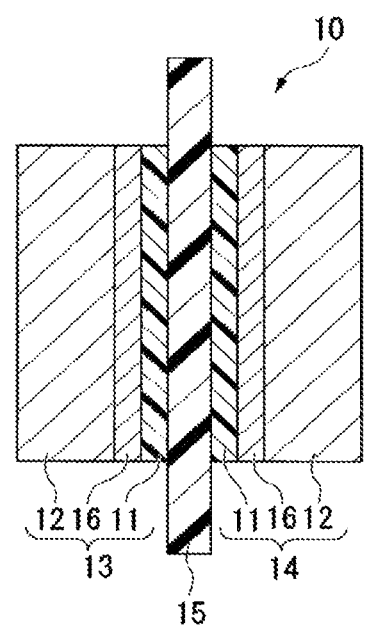
FIG. 2 is a schematic cross-sectional view showing another example of the membrane/electrode assembly of the present invention.

As shown in FIG. 2, the membrane/electrode assembly 10 may have a carbon layer 16 between the catalyst layer 11 and the gas diffusion layer 12.

When the membrane/electrode assembly 10 is provided with a carbon layer, the gas diffusion property at a surface of the catalyst layer improves, and the power generation performance of a polymer electrolyte fuel cell remarkably improves.

The carbon layer is a layer comprising carbon and a nonionic fluorinated polymer.

As the carbon, carbon particles or carbon fibers may be mentioned, and carbon nanofibers having a fiber diameter of from 1 to 1,000 nm and a fiber length of at most 1,000 μm are preferred. As the nonionic fluorinated polymer, a polytetrafluoroethylene or the like may be mentioned.

The polymer electrolyte membrane is a membrane comprising a polymer having ion exchange groups.

The polymer having an ion exchange group may, for example, be the polymer H or a perfluoropolymer having an ion exchange group other than the polymer H. The ion exchange group in the polymer contained in the polymer electrolyte membrane is preferably acid form, and preferably an acid form sulfonic acid group.

The polymer electrolyte membrane may be reinforced with a reinforcing material. The material of the reinforcing material is as described above.

The polymer electrolyte membrane may contain a metal, a metal compound or metal ions of at least one member selected from the group consisting of cerium and manganese, in order to further improve the durability. Cerium and manganese decompose hydrogen peroxide or hydroxy radicals and hydroperoxy radicals which are causative substances causing the deterioration of the polymer electrolyte membrane. Cerium and manganese are preferably present in the polymer electrolyte membrane as ions, and so long as they are present as ions, they may be present in any state in the polymer electrolyte membrane. As the method of incorporating cerium or manganese in a polymer electrolyte membrane, a method of immersing the polymer electrolyte membrane in an aqueous solution containing cerium or manganese or a method of obtaining a polymer electrolyte membrane from a liquid composition containing cerium or manganese may be mentioned.

In a case where the membrane/electrode assembly has no carbon layer, the membrane/electrode assembly may be produced, for example, by the following methods.

A method of forming a catalyst layer on a polymer electrolyte membrane to produce a membrane/catalyst layer assembly and sandwiching the membrane/catalyst layer assembly between gas diffusion layers.

A method of forming a catalyst layer on a gas diffusion layer to produce electrodes (anode and cathode) and sandwiching a polymer electrolyte membrane between the electrodes.

In a case where the membrane/electrode assembly has a carbon layer, the membrane/electrode assembly may be produced, for example, by the following methods.

A method of applying a dispersion containing carbon and a nonionic fluorinated polymer on a substrate film, followed by drying to form a carbon layer, forming a catalyst layer on the carbon layer, bonding the catalyst layer and a polymer electrolyte membrane, peeling the substrate film to produce a membrane/catalyst layer assembly having a carbon layer, and sandwiching the membrane/catalyst layer assembly between gas diffusion layers.

A method of applying a dispersion containing carbon and a nonionic fluorinated polymer on a gas diffusion layer, followed by drying to form a carbon layer, and sandwiching a membrane/catalyst layer assembly having a carbon layer formed on a polymer electrolyte membrane between gas diffusion layers having a carbon layer.

The method for forming a catalyst layer may, for example, be the following method.

A method of applying a catalyst layer-forming coating liquid on a polymer electrolyte membrane, a gas diffusion layer or a carbon layer, followed by drying.

A method of applying a catalyst layer-forming coating liquid on a substrate film, followed by drying to form a catalyst layer and transferring the catalyst layer on a polymer electrolyte membrane.

The catalyst layer-forming coating liquid is a liquid having a polymer having an ion exchange group and a catalyst dispersed in a dispersion medium. For example, the catalyst layer-forming coating liquid is prepared by mixing the liquid composition of the present invention and a dispersion of a catalyst. The catalyst layer-forming coating liquid may contain a metal, a metal compound or metal ions of at least one member selected from the group consisting of cerium and manganese, in order to improve the durability of a catalyst layer.

The polymer electrolyte membrane is formed, for example, by a method (cast method) of applying a liquid composition on a substrate film or a catalyst layer, followed by drying.

The liquid composition is a dispersion having a polymer having an ion exchange group dispersed in a dispersion medium containing water and an organic solvent. As the liquid composition, the liquid composition of the present invention may be used.

The polymer electrolyte membrane is preferably subjected to annealing treatment for stabilization. The annealing treatment temperature is preferably from 130 to 200° C., although it varies depending on the type of the fluorinated polymer having an ion exchange group. When the annealing treatment temperature is at least 130° C., the polymer having an ion exchange group tends not to excessively absorb water. When the annealing treatment temperature is at most 200° C., the thermal decomposition of the ion exchange group is suppressed.

In the membrane/electrode assembly of the present invention, at least one selected from the group consisting of the catalyst layer of the cathode, the catalyst layer of the anode and the polymer electrolyte membrane comprises the polymer H having a high ion exchange capacity and a high mechanical strength at a high temperature and being inexpensive as compared with conventional one, whereby the power generation performance is excellent, and the polymer electrolyte membrane or the catalyst layer has a high mechanical strength at a high temperature, and the membrane/electrode assembly is inexpensive as compared with conventional one.

(Polymer Electrolyte Fuel Cell)

The polymer electrolyte fuel cell of the present invention has the membrane/electrode assembly of the present invention.

The polymer electrolyte fuel cell of the present invention may have separators having grooves to be gas flow paths formed, on both surfaces of the membrane/electrode assembly. The separator may, for example, be a separator made of a conductive material such as a separator made of a metal, a separator made of carbon, and a separator made of a material in which graphite and resin are mixed.

In the polymer electrolyte fuel cell, gas containing oxygen is supplied to the cathode, and gas containing hydrogen is supplied to the anode to generate electricity. Further, the membrane/electrode assembly may be applicable also to a methanol fuel cell which generates electricity by supplying methanol to the anode.

The polymer electrolyte fuel cell of the present invention has the membrane/electrode assembly of the present invention wherein at least one selected from the group consisting of the catalyst layer of the cathode, the catalyst layer of the anode and the polymer electrolyte membrane comprises the polymer H having a high ion exchange capacity and a high mechanical strength at a high temperature and being inexpensive as compared with conventional one, whereby the power generation performance is excellent, and the polymer electrolyte membrane or the catalyst layer has a high mechanical strength at a high temperature, and the polymer electrolyte fuel cell is inexpensive as compared with conventional one.

(Cation Exchange Membrane for Alkali Chloride Electrolysis)

The cation exchange membrane for alkali chloride electrolysis of the present invention may contain the polymer H or may be a laminate of a layer containing the polymer H and a layer containing a polymer having a carboxylic acid group. The cation exchange group (sulfonic acid group or carboxylic acid group) is preferably salt form.

The cation exchange membrane for alkali chloride electrolysis of the present invention comprises the polymer H having a high ion exchange capacity and a high mechanical strength at a high temperature and being inexpensive as compared with conventional one, whereby the overvoltage of a membrane resistance or the like in alkali chloride electrolysis can be reduced, and the electric power consumption rate can be reduced, the mechanical strength at a high temperature is high, and it is inexpensive as compared with conventional one.

(Ion Exchange Membrane for Water Electrolysis)

The ion exchange membrane for water electrolysis of the present invention comprises the polymer H or has a layer containing the polymer H and is used as either of an ion exchange membrane for alkali water electrolysis and an ion exchange membrane for polymer electrolyte water hydrolysis. In the case of the alkali water hydrolysis, the sulfonic acid group in the polymer H is preferably a salt form, and in the case of the polymer electrolyte water hydrolysis, the sulfonic acid group in the polymer H is preferably acid form.

The ion exchange membrane for water electrolysis of the present invention comprises the polymer H having a high ion exchange capacity and a high mechanical strength at a high temperature and being inexpensive as compared with conventional one, whereby overvoltage of a membrane resistance or the like in water electrolysis can be reduced, and the electric power consumption rate can be reduced, the mechanical strength at a high temperature is high, and it is inexpensive as compared with conventional one.

(Diaphragm for Redox Flow Secondary Cell)

The diaphragm for a redox flow secondary cell of the present invention comprises the polymer H or has a layer containing the polymer H. The sulfonic acid group in the polymer H is preferably acid form.

The diaphragm for a redox flow secondary cell of the present invention comprises the polymer H having a high ion exchange capacity and a high mechanical strength at a high temperature and being inexpensive as compared with conventional one and thereby has a high proton permeability, a low ion transport resistance and a high mechanical strength at a high temperature and is inexpensive as compared with conventional one.

(Ion Exchange Membrane for Electrochemical Hydrogen Pump)

The ion exchange membrane for an electrochemical hydrogen pump of the present invention comprises the polymer H or has a layer containing the polymer H. The sulfonic acid group in the polymer H is preferably acid form.

The ion exchange membrane for an electrochemical hydrogen pump of the present invention comprises the polymer H having a high ion exchange capacity and a high mechanical strength at a high temperature and being inexpensive as compared with conventional one, and thereby has a low electric power consumption rate for proton transport or raising hydrogen pressure and a high mechanical strength at a high temperature and is inexpensive as compared with conventional one.

(Acid Form Sulfonic Acid Group-Containing Fluorocarbon Polymer)

The acid form sulfonic acid group-containing fluorocarbon polymer of the present invention has a hydrogen gas permeability coefficient of at most $2.9 \times 10^{-9}$ cm$^3$·cm/(s·cm$^2$·cmHg) (hereinafter, unit may sometimes be omitted) under conditions of a temperature of 80° C. and a relative humidity of 10%. When this polymer is used in a polymer electrolyte membrane for a polymer electrolyte fuel cell, advantageous effects are obtained such that the leak amount of hydrogen gas is reduced, and the fuel consumption rate is thereby low, and cell voltage improves. Further, when this polymer is used in an ion exchange membrane for water electrolysis, the amount of oxygen included in hydrogen to be formed or the amount of hydrogen included in oxygen to be formed decreases, whereby safety improves. Further, with a small film thickness as compared with conventional membranes, hydrogen can be blocked at the same level as conventional membranes, whereby electrolytic voltage can be reduced, which results in the decrease of the electric power consumption rate or the improvement of the output density. Further, in a case where the polymer is used in an ion exchange membrane for an electrochemical hydrogen pump, the reverse osmosis of compressed hydrogen is suppressed, whereby the electric power consumption rate required for compression can be reduced.

The acid form sulfonic acid group-containing fluorocarbon polymer of the present invention has a hydrogen gas permeability coefficient under conditions of a temperature of 80° C. and a relative humidity of 10%, of preferably at most $2.9 \times 10^{-9}$, more preferably at most $2.5 \times 10^{-9}$, further preferably at most $2.3 \times 10^{-9}$, most preferably at most $1.8 \times 10^{-9}$. On the other hand, in order to achieve the ion conductivity also, the hydrogen gas permeability coefficient is preferably at least $1.0 \times 10^{-12}$, more preferably at least $1.0 \times 10^{-11}$.

With a view to securing a sufficient ion conductivity, in order from the preferred range to the more preferred range, the ion exchange capacity of the acid form sulfonic acid group-containing fluorocarbon polymer of the present invention is at least 0.9, at least 1.0, at least 1.1, at least 1.2, most preferably at least 1.3. On the other hand, with a view to suppressing swelling of the polymer and securing the mechanical strength, it is preferably at most 2.5, more preferably at most 2.4, further preferably at most 2.3.

The acid form sulfonic acid group-containing fluorocarbon polymer of the present invention is produced, for example, by controlling the composition, the molecular weight, the ion exchange capacity, etc. of the polymer H. The acid form sulfonic acid group-containing fluorocarbon polymer of the present invention is preferably a perfluoropolymer. "Perfluoropolymer" means that all monomer units constituting the polymer are based on perfluoromonomers. Here, "perfluoromonomer" means a monomer of which all hydrogen atoms bonded to carbon atoms are substituted by fluorine atoms.

(Polymer Electrolyte Membrane)

The polymer electrolyte membrane according to another embodiment of the present invention comprises the acid form sulfonic acid group-containing fluorocarbon polymer of the present invention.

The polymer electrolyte membrane of the present invention has a thickness of preferably from 5 to 200 μm, more preferably from 10 to 130 μm. When the thickness is at most the upper limit value of the above range, the membrane resistance can be sufficiently lowered. When the thickness is at least the lower limit value of the above range, a sufficient hydrogen gas barrier property can be secured.

The polymer electrolyte membrane of the present invention can be produced by the same method for producing the membrane comprising the polymer H of the present invention, and as the case requires, the same treatment or the same reinforcement may be carried out, or the same additive may be added.

EXAMPLES

Now, the present invention will be described in detail with reference to Examples, but the present invention is not limited thereto.

Ex. 1 is a Production Example, Ex. 2, 3, 6, 8, 10 and 11 are Examples of the present invention, and Ex. 4, 5, 7, 9 and 12 are Comparative Examples. Physical properties, etc. of the following polymers and other polymers are similarly measured.

($^1$H-NMR)

$^1$H-NMR was measured under conditions of frequency of 300.4 MHz and chemical shift reference of tetramethylsilane. Unless otherwise specified, CD$_3$CN was used as a solvent. The quantitative measurement of a product was conducted by results of $^1$H-NMR analysis and the amount of an added internal standard sample (1,3-bis(trifluoromethyl)benzene).

($^{19}$F-NMR)

$^{19}$F-NMR was measured under conditions of frequency of 282.7 MHz, a solvent of CD$_3$CN and chemical shift reference of CFCl$_3$. The quantitative measurement of a product was conducted by results of $^{19}$F-NMR and the amount of an added internal standard sample (1,3-bis(trifluoromethyl)benzene).

($^{13}$C-NMR)

$^{13}$C-NMR was measured under conditions of frequency of 75.5 MHz and chemical shift reference of tetramethylsilane. Unless otherwise specific, CD$_3$CN was used as a solvent.

(Yield)

The yield is (yield of a reaction step)×(yield of a purification step), and the reaction yield is the yield of a reaction step before purifying a desired product, which excludes the loss in the purification step.

(Ion Exchange Capacity)

The ion exchange capacity (meq/g dry resin) of the polymer H was obtained as follows.

A membrane of a polymer F was vacuum dried at 120° C. for 12 hours. The mass of the dried membrane of the polymer was measured, and then the membrane of the polymer was immersed in a 0.85 mol/g sodium hydroxide solution (solvent: water/methanol=10/90 (mass ratio)) at 60° C. for 72 hours or longer to hydrolyze ion exchange groups. The sodium hydroxide solution after the hydrolysis was back titrated with 0.1 mol/L hydrochloric acid to obtain the ion exchange capacity.

(Proportion of Units Based on Fluorosulfonyl Group-Containing Monomer)

The proportions of units based on the fluorosulfonyl group-containing monomer (SO$_2$F group-containing monomer) in the polymer F was calculated from the ion exchange capacity of the polymer F.

(TQ Value)

The polymer F was melt extruded by means of a flow tester (CFT-500A, manufactured by Shimadzu Corporation) provided with a nozzle having a length of 1 mm and an internal diameter of 1 mm under an extrusion pressure of 2.94 MPa (gage pressure) while changing the temperature. The temperature (TO value) at which the extruded amount of the polymer F became 100 mm³/s was obtained. The higher the TQ value is, the larger the molecular weight of the polymer is.
(Dynamic Viscoelasticity)

The dynamic viscoelasticity of the membrane of the polymer F or the membrane of the polymer H was measured by means of a dynamic viscosity measuring apparatus (DVA-225, manufactured by IT Keisoku Seigyo) under conditions of test specimen width: 5.0 mm, length of specimen between grips: 15 mm, measuring frequency: 1 Hz, rate of temperature rise: 2° C./min and a tensile mode. Tan σ (loss tangent) was calculated from the ratio (E"/E') of the loss elastic modulus E" to the storage elastic modulus E', and tan σ-temperature curve was drawn. The value of a peak temperature between −100 to 200° C. on the tan σ-temperature curve is Tg of the polymer F or a softening temperature of the polymer H. Further, a storage elastic modulus E'-temperature curve was drawn, and a value of the storage elastic modulus at 120° C. was taken as a 120° C. storage elastic modulus of the polymer H.
(Conductivity)

To a membrane of the polymer H having a thickness of 25 µm and a width of 5 mm, a substrate provided with 4 terminal electrodes at an interval of 5 mm was contact-bonded by a known four probe method, and the resistance of the membrane of the polymer H was measured at an alternative current: 10 kHz and a voltage: 1 V under the constant temperature and constant humidity conditions of temperature: 80° C. and relative humidity of 50% to calculate the conductivity.
(Moisture Content)

The membrane of the polymer H was immersed in warm water of 80° C. for 16 hours and cooled until the water temperature reached at most 25° C. The membrane of the polymer H was taken out, water droplets attached on a surface of the membrane were wiped away by a filter paper, and the mass W1 of the membrane of the polymer H was measured. The membrane of the polymer H was dried in a glove box under a nitrogen atmosphere for 48 hours, and then the mass W2 of the membrane of the polymer H was measured in the glove box. The moisture content (mass standard) was obtained by the following formula I.

Moisture content=(W1−W2)/W2×100     Formula 1

(Hydrogen Gas Permeability Coefficient 1)

The hydrogen gas permeability coefficient of a polymer electrolyte membrane comprising the acid form sulfonic acid group-containing fluorocarbon polymer was measured in accordance with JIS K7126-2:2006. As the measuring apparatus, a gas permeability measuring apparatus (GTR-100XFAG, manufactured by GTR Tec Corporation) was used.

The amount of hydrogen gas permeation converted to a volume at 25° C. at 1 atm was measured by maintaining a polymer electrolyte membrane having an effective permeable area of 9.62 cm² at 80° C., flowing hydrogen gas of which the relative humidity was controlled to 10% to a first face at 30 mL/min, flowing argon gas of which the relative humidity was controlled to 10% to a second face at 30 mL/min and detecting hydrogen gas permeating into argon gas by gas chromatography. The permeability of gas permeating in one second in a membrane area of 1 cm² per pressure difference of permeating gas of 1 cmHg was obtained from the obtained amount of hydrogen gas permeation, and a value converted to a membrane having a thickness of 1 cm was taken as hydrogen gas permeability coefficient 1.

(Hydrogen Gas Permeability Coefficient 2)

The hydrogen gas permeability coefficient 2 was obtained as a value measured in the same manner as in the hydrogen gas permeability coefficient 1, except that the relative humidity of hydrogen gas flowed to the first face was controlled to 20%.
(Abbreviations)

PSVE: $CF_2=CFOCF_2CF(CF_3)OCF_2CF_2SO_2F$,
P2SVE: $CF_2=CFOCF_2CF(CF_2OCF_2CF_2SO_2F)OCF_2CF_2SO_2F$,
sPSVE: $CF_2=CFOCF_2CF_2SO_2F$,
PFtBPO: $(CF_3)_3COOC(CF_3)_3$,
AIBN: $(CH_3)_2C(CN)N=NC(CH_3)_2(CN)$,
IPP: $(CH_3)_2CHOC(O)OOC(O)OCH(CH_3)_2$,
V-601: $CH_3OC(O)C(CH_3)_2-N=N-C(CH_3)_2C(O)OCH_3$,
HFC-52-13p: $CF_3(CF_2)_5H$,
HFE-347pc-f: $CF_3CH_2OCF_2CF_2H$,
HCFC-225cb: $CClF_2CF_2CHClF$,
HCFC-141b: $CH_3CCl_2F$.

Ex. 1

Ex. 1-1

560 g of chlorosulfuric acid was charged in a 2 L four-necked flask provided with a stirrer, a condenser, a thermometer and a dropping funnel under nitrogen gas sealing. The flask was cooled in an ice bath, and a mixed liquid of 139.5 g of the compound 1-1 and 478.7 g of dichloromethane was dropwise added over 20 minutes, while maintaining the internal temperature at 20° C. Heat generation and generation of gas were observed at the time of the dropwise addition. After completion of the dropwise addition, the flask was set in an oil bath, and a reaction was carried out for 7 hours while maintaining the internal temperature at from 30 to 40° C. The reaction proceeded with the generation of gas, and a white solid precipitated. After the reaction, the inside of the flask was decompressed to distill dichloromethane off. A yellowish white solid remained in the flask. The solid was analyzed by ¹H-NMR, and formation of compound 2-1 was confirmed.

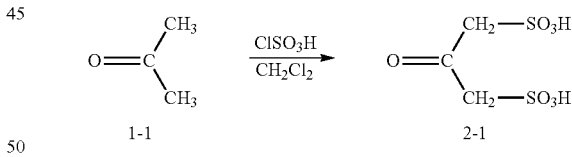

NMR spectrum of compound 2-1:
¹H-NMR (solvent: D₂O): 4.27 ppm (—CH₂—, 4H, s).
¹³C-NMR (solvent: D₂O): 62.6 ppm (—CH₂—), 195.3 ppm (C=O).

Ex. 1-2

The compound 2-1 obtained in Ex. 1-1 was used in a subsequent reaction as it was without being isolated. 2,049 g of thionyl chloride was added in the flask of Ex. 1-1. The flask was heated to 80° C., followed by reflux for 15 hours. Along with the progress of the reaction, the reflux temperature increased from 52° C. to 72° C. The generation of gas was observed during the reaction. The termination of the reaction was when the compound 2-1 was entirely dissolved, and the generation of gas terminated. The reaction liquid was transferred to a 2 L separable flask, and the flask was left to cool for 9 hours while a gas phase part was sealed with nitrogen gas, and as a result, a blackish brown solid precipitated in the separable flask. Unreacted thionyl chloride was removed by decantation. Toluene was added to wash the precipitated solid, and toluene was removed by decantation again. Washing with toluene was carried out three times in total, and the amount of used toluene was 1,207 g in total. The precipitated solid was dried at 25° C. for 71 hours under nitrogen gas stream. The dried solid was recovered and analyzed by $^1$H-NMR, and it was confirmed that 356.5 g of compound 3-1 with a purity of 96.2% was obtained. The yield on the compound 1-1 basis was 56.0%.

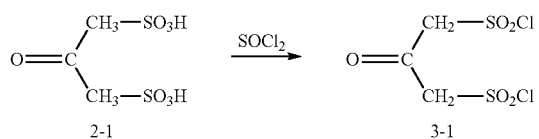

NMR spectrum of compound 3-1:
$^1$H-NMR: 5.20 ppm (—CH$_2$—, 4H, s).
$^{13}$C-NMR: 72.3 ppm (—CH$_2$—), 184.6 ppm (C=O).

Ex. 1-3

90.0 g of the compound 3-1 and 750 mL of acetonitrile were charged in a 1 L four-necked flask provided with a stirrer, a condenser and a thermometer under nitrogen gas sealing. The flask was cooled in an ice bath, and 110.3 g of potassium hydrogen fluoride was added with stirring. Heat generation due to the addition was slight. The ice bath was changed to a water bath, and a reaction was carried out for 62 hours while maintaining the internal temperature at from 15 to 25° C. Along with the reaction, fine white solids formed. The reaction liquid was transferred to a pressure filter, and unreacted potassium hydrogen fluoride was removed from the product by filtration. Acetonitrile was added to the filter, the solid remaining on the filter was washed until the filtrate became transparent, and the wash was recovered. The filtrate and the wash were subjected to an evaporator to distill acetonitrile off. 950 mL of toluene was added to the remaining dried solid, followed by heating to 100° C. to dissolve the solid in toluene. The solution was natural filtered to remove undissolved components. The filtrate was transferred to a 1 L separable flask, and the flask was left to cool for 14 hours while a gas phase part was sealed with nitrogen gas, and as a result, pale brown needle crystals precipitated in the separable flask. The crystals were washed with toluene and dried at 25° C. for 30 hours under nitrogen gas stream. The dried solid was recovered and analyzed by $^1$H-NMR and $^{19}$F-NMR, and as a result, it was confirmed that 58.1 g of compound 4-1 with a purity of 97.6% was obtained. The yield on the compound 3-1 basis was 72.3%.

NMR spectrum of compound 4-1:
$^1$H-NMR: 4.97 ppm (—CH$_2$—, 4H, d, J=3.1 Hz).
$^{19}$F-NMR: 62.4 ppm (—SO$_2$F, 2F, t, J=3.1 Hz).
$^{13}$C-NMR: 60.7 ppm (—CH$_2$—), 184.9 ppm (C=O).

Ex. 1-4

9.93 g of the compound 4-1 and 89.7 g of acetonitrile were charged in a 200 mL autoclave made of nickel. The autoclave was cooled, nitrogen gas was fed at a flow rate of 6.7 L/hr while maintaining the internal temperature at from 0 to 5° C., and the reaction liquid was bubbled for 1 hours. While maintaining the temperature of the reaction liquid at from 0 to 5° C., a mixed gas of fluorine gas and nitrogen gas (mixing ratio=10.3 mol %/89.7 mol %) was introduced over 6 hours at a flow rate of 6.7 L/hr. Nitrogen gas was fed again at a flow rate of 6.7 L/hr, and the reaction liquid was bubbled for 1 hour. 103.2 g of the reaction liquid was recovered from the autoclave. The reaction liquid was analyzed by $^{19}$F-NMR, and it was confirmed that 8.4 mass % of compound 5-1 was contained. The reaction yield on the compound 4-1 basis was 66%.

NMR spectrum of compound 5-1:
$^{19}$F-NMR: −104.1 ppm (—CF$_2$—, 4F, s), 45.8 ppm (—SO$_2$F, 2F, s).

Ex. 1-5

19.9 g of the compound 4-1 and 85.6 g of acetonitrile were charged in a 200 mL autoclave made of nickel. The autoclave was cooled, nitrogen was fed at a flow rate of 6.7 L/hr while maintaining the internal temperature at from 0 to 5° C., and the reaction liquid was bubbled for 1 hour. While maintaining the temperature of the reaction liquid at from 0 to 5° C., a mixed gas of fluorine gas and nitrogen gas (mixing ratio=10.3 mol %/89.7 mol %) was introduced at a flow rate of 16.4 L/hr over 6.5 hours. Nitrogen gas was fed again at a flow rate of 6.7 L/hr, and the reaction liquid was bubbled for 1 hour. 109.6 g of the reaction liquid containing the compound 5-1 was recovered from the autoclave.

Ex. 1-6

20.1 g of the compound 4-1 and 80.1 g of acetonitrile were charged in a 200 mL autoclave made of nickel. The autoclave was cooled, nitrogen gas was fed at a flow rate of 6.7 L/hr while maintaining the internal temperature at from 0 to 5° C., and the reaction liquid was bubbled for 1 hour. While maintaining the temperature of the reaction liquid at from 0 to 5° C., a mixed gas of fluorine gas and nitrogen gas (mixing ratio=20.0 mol %/80.0 mol %) was introduced at a flow rate of 8.4 L/hr over 6 hours. Nitrogen gas was fed again at a flow rate of 6.7 L/hr, and the reaction liquid was bubbled for 1 hour. 107.1 g of the reaction liquid containing the compound 5-1 was recovered from the autoclave.

Ex. 1-7

1.65 g of potassium fluoride and 7.8 mL of diethylene glycol dimethyl ether (diglyme) were charged in a 50 mL four-necked flask provided with a stirrer, a condenser, a thermometer and a dropping funnel. The flask was cooled in an ice bath, and 8.43 g of the reaction liquid obtained in Ex. 1-4 was dropwise added by means of a plastic syringe while maintaining the internal temperature at from 0 to 10° C. by stirring. Intense heat generation was observed, and 15 minutes was spent for the dropwise addition. After completion of the dropwise addition, the ice bath was changed to a water bath, and the reaction was carried out for 1 hour at from 15 to 20° C. The flask was cooled in an ice bath again, and 6.56 g of compound 6-1 was dropwise added from a dropping funnel while maintaining the temperature of the reaction liquid at from 0 to 10° C. After completion of the dropwise addition, the ice bath was changed to a water bath, and the reaction was carried out for 3.5 hours at from 20 to 25° C. By-products were removed from the reaction liquid by suction filtration to recover the filtrate. The solid removed by filtration was washed with an appropriate amount of acetonitrile, and the wash and the filtrate were mixed. 37.1 g of the filtrate was quantitatively analyzed by $^{19}$F-NMR, and it was confirmed that 2.04 mass % of compound 7-1 was contained. The reaction yield on the compound 4-1 basis was 46.6%.

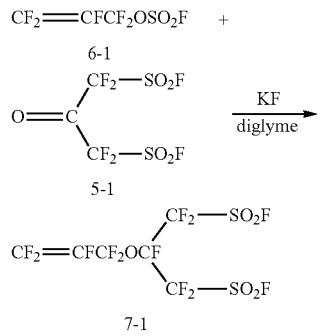

NMR spectrum of compound 7-1:
$^{19}$F-NMR: −191.5 ppm ($CF_2$=CF—, 1F, ddt, J=116, 38, 14 Hz), −133.8 ppm (—O—CF—, 1F, tt, J=21.3, 6.1 Hz), −103.1 ppm (—$CF_2$—$SO_2$F, 4F, m), −101.5 ppm ($CF_2$=CF—, 1F, ddt, J=116, 49, 27 Hz), −87.6 ppm ($CF_2$=CF—, 1F, ddt, J=49, 38, 7 Hz), −67.5 ppm (—$CF_2$—O—, 2F, m), 46.8 ppm (—$SO_2$F, 2F, s).

Ex. 1-8

36.6 g of potassium fluoride and 125.6 g of acetonitrile were charged in a 500 mL four-necked flask provided with a stirrer, a condenser, a thermometer and a dropping funnel. The flask was cooled in an ice bath, and 79.8 g of the reaction liquid obtained in Ex. 1-5 was dropwise added by means of a dropping funnel made of a plastic while maintaining the internal temperature at from 0 to 10° C. by stirring. Intense heat generation was observed, and 23 minutes was spent for the dropwise addition. After completion of the dropwise addition, the ice bath was changed to a water bath, and the reaction was carried out for 5.5 hour at from 20 to 30° C. The flask was cooled in an ice bath again, and 146.0 g of the compound 6-1 was dropwise added from a dropping funnel while maintaining the temperature of the reaction liquid at from 0 to 10° C. After completion of the dropwise addition, the ice bath was changed to a water bath, and the reaction was carried out for 16 hours at from 15 to 25° C. Suction filtration was carried out in the same manner as in Ex. 7-1, and 412.3 g of the obtained filtrate was quantitatively analyzed by $^{19}$F-NMR, and it was confirmed that 3.93 mass % of the compound 7-1 was contained. The reaction yield on the compound 4-1 basis was 55.9%. The filtrate was distilled off under reduced pressure to isolate the compound 7-1 as a fraction with a boiling point of 97.2° C./10 KPa. The purity by gas chromatography was 98.0%.

Ex. 1-9

3.70 g of potassium fluoride and 10.9 g of acetonitrile were charged in a 50 mL four-necked flask provided with a stirrer, a condenser, a thermometer and a dropping funnel. The flask was cooled in an ice bath, and 10.2 g of the reaction liquid obtained in Ex. 1-6 was dropwise added by means of a plastic syringe while maintaining the internal temperature at from 0 to 10° C. by stirring. Intense heat generation was observed, and 8 minutes was spent for the dropwise addition. After completion of the dropwise addition, the ice bath was changed to a water bath, and the reaction was carried out for 3 hours at from 20 to 30° C. The flask was cooled in an ice bath again, and 14.6 g of the compound 6-1 was dropwise added from a dropping funnel while maintaining the temperature of the reaction liquid at from 0 to 10° C. After completion of the dropwise addition, the ice bath was changed to a water bath, and the reaction was carried out for 17 hours at from 15 to 25° C. Suction filtration was carried out in the same manner as in Ex. 7-1, and 55.9 g of the obtained filtrate was quantitatively analyzed by $^{19}$F-NMR, and it was confirmed that 4.77 mass % of the compound 7-1 was contained. The reaction yield on the compound 4-1 basis was 69.6%. Further, the reaction yield on the compound 1-1 basis (the reaction yield in all steps for preparing the monomer) was 28.2%.

Ex. 2

Ex. 2-1

70.0 g of the compound 7-1 was added in an autoclave (internal capacity of 100 mL and made of stainless steel), followed by cooling and deaerating by liquid nitrogen. 2.53 g of TFE was introduced in the autoclave, and the autoclave was heated in an oil bath until the internal temperature reached 100° C. The pressure at that time was 0.29 MPaG (gage pressure). A mixed liquid of 36.3 mg of PFtBPO as a polymerization initiator and 2.58 g of HFC-52-13p was injected into the autoclave. Further, nitrogen gas was introduced from an injection line to completely inject the liquid in the injection line into the autoclave. TFE in the gas phase part was diluted by this operation, and as a result, the pressure increased to 0.56 MPaG. While maintaining the pressure at 0.56 MPaG, TFE was continuously added to carry out polymerization. The inside of the autoclave was cooled to terminate the polymerization, when the added amount of TFE reached 4.03 g after 9.5 hours, and the gas in the system was purged. The reaction liquid was diluted with HFC-52-13p, HFE-347pc-f was added to aggregate the polymer, and the polymer was filtered. Then, an operation of stirring the polymer in HFC-52-13p and aggregating the polymer with HFE-347pc-f again was repeated twice. Vacuum drying at 120° C. was carried out to obtain polymer F-1 which is a copolymer of TFE and the compound 7-1. Results are shown in Table 1.

Ex. 2-2 to Ex. 2-5

Polymer F-2 to polymer F-5 were obtained in the same manner as in Ex. 2-1, except that conditions were changed as shown in Table 1 (in Ex. 2-2, 34.0 g of HFC-52-13p was charged with the compound 7-1, and 2.9 g was used to prepare a mixed liquid with the polymerization initiator, and in Ex. 2-3 to Ex. 2-5, without initially charging TFE, and instead, after heating to the polymerization temperature, TFE was injected until the pressure reached the pressure prior to nitrogen gas dilution as shown in Table 1). Results are shown in Table 1.

Ex. 3

Ex. 3-1 to Ex. 3-5

Membranes of polymers H-1 to H-5 were obtained by the following method using the above obtained polymers F-1 to F-5.

A polymer F was press molded at a temperature higher by 10° C. than TQ value (260° C. in Ex. 3-4 and Ex. 3-5) under 4 MPa (gage pressure) to obtain a membrane (thickness of from 100 to 250 μm) of the polymer F. The membrane of the polymer F was immersed in an alkali aqueous solution as shown in Table 2 at 80° C. for 16 hours to hydrolyze and thereby convert —$SO_2F$ groups in the polymer F into —$SO_3K$ groups. Further, the membrane of the polymer was immersed in a 3 mol/L hydrochloric acid aqueous solution at 50° C. for 30 minutes and then immersed in ultrapure water at 80° C. for 30 minutes. A cycle of immersing in a hydrochloric acid aqueous solution and immersing in ultrapure water was carried out five times in total to convert —$SO_3K$ groups in the polymer into —$SO_3H$ groups. The washing with ultrapure water was repeated, until pH of water in which the membrane of the polymer was immersed became 7. The membrane of the polymer was sandwiched between filter papers and air-dried to obtain a membrane of polymer H. Results are shown in Table 2.

TABLE 1

|  | Ex. 2-1 | Ex. 2-2 | Ex. 2-3 | Ex. 2-4 | Ex. 2-5 |
| --- | --- | --- | --- | --- | --- |
| Obtained polymer F | F-1 | F-2 | F-3 | F-4 | F-5 |
| Capacity of reactor [mL] | 100 | 100 | 100 | 100 | 100 |
| Compound 7-1 [g] | 70.0 | 31.5 | 103.0 | 80.0 | 82.0 |
| Initially charged TFE [g] | 2.53 | 2.44 | — | — | — |
| HFC-52-13p [g] | 2.58 | 36.9 | 6.46 | 4.23 | 4.18 |
| Polymerization initiator | PFtBPO | PFtBPO | PFtBPO | PFtBPO | PFtBPO |
| Amount of polymerization initiator [mg] | 36.3 | 34.3 | 105.8 | 41.4 | 42.3 |
| Polymerization temperature [° C.] | 100 | 100 | 100 | 100 | 100 |
| Pressure prior to nitrogen gas dilution [MPaG] | 0.29 | 0.27 | 0.10 | 0.29 | 0.25 |
| Polymerization pressure [MPaG] | 0.56 | 0.56 | 0.60 | 0.56 | 0.49 |
| Continuously added TFE [g] | 4.03 | 4.29 | 3.84 | 5.59 | 6.49 |
| Polymerization time [hr] | 9.5 | 8.5 | 12.5 | 6.9 | 10.0 |
| Yield of polymer F [g] | 6.4 | 4.6 | 7.61 | 8.47 | 10.0 |
| Ion exchange capacity [meq/g dry resin] | 1.87 | 1.49 | 2.37 | 1.78 | 1.90 |
| Units based on compound 7-1 [mol %] | 13.8 | 10.0 | 19.9 | 12.4 | 14.0 |
| Units based on compound 7-1 [mass %] | 41.5 | 33.0 | 52.5 | 38.6 | 42.1 |
| TQ value [° C.] | 238 | 268 | 158 | 298 | 314 |
| Tg [° C.] | 39 | 43 | 33 | 41 | 39 |

TABLE 2

|  | Ex. 3-1 | Ex. 3-2 | Ex. 3-3 | Ex. 3-4 | Ex. 3-5 |
| --- | --- | --- | --- | --- | --- |
| Used polymer F | F-1 | F-2 | F-3 | F-4 | F-5 |
| Obtained polymer H | H-1 | H-2 | H-3 | H-4 | H-5 |
| Used alkali aqueous solution | Aqueous solution A | Aqueous solution B | Aqueous solution A | Aqueous solution C | Aqueous solution A |
| Softening temperature [° C.] | 147 | 151 | 151 | 151 | 153 |
| Conductivity [S/cm] | 0.136 | 0.080 | 0.164 | 0.123 | 0.136 |
| Elastic modulus at 120° C. [MPa] | 95.7 | 160 | 72.1 | 119 | 117 |
| Moisture content [%] | 136 | 48 | At least 400 | 93 | 110 |

In Table 2, "aqueous solution A" is potassium hydroxide/water=20/80 (mass ratio), "aqueous solution B" is potassium hydroxide/dimethylsulfoxide/water=15/30/55 (mass ratio), and "aqueous solution C" is potassium hydroxide/methanol/water=15/20/65 (mass ratio). Further, these definitions are also applied to the after-described Table 4.

Ex. 4

Ex. 4-1

123.8 g of PSVE, 35.2 g of HCFC-225cb and 63.6 mg of AIBN were added in a hastelloy autoclave having an internal capacity of 230 mL, followed by cooling and deaeration by liquid nitrogen. The temperature was raised to 70° C., and TFE was introduced in the system to maintain the pressure at 1.14 MPaG. TFE was continuously added so as to maintain the constant pressure at 1.14 MPaG. After 7.9 hours, when the amount of added TFE reached 12.4 g, the autoclave was cooled, and gas in the system was purged to terminate the reaction. The polymer solution was diluted with HCFC-225cb, and HCFC-141b was added for aggregation. Washing with HCFC-225cb and HCFC-141b was carried out, followed by drying to obtain 25.1 g of polymer F'-1 which is a copolymer of TFE and PSVE. Results are shown in Table 3.

Ex. 4-2 to Ex. 4-4

TFE and PSVE or P2SVE were copolymerized in the same manner as in Ex. 4-1 to obtain polymers F'-2 to F'-4, except that respective conditions were changed as shown in Table 3. Results are shown in Table 3.

TABLE 3

|  | Ex. 4-1 | Ex. 4-2 | Ex. 4-3 | Ex. 4-4 |
| --- | --- | --- | --- | --- |
| Obtained polymer F | F'-1 | F'-2 | F'-3 | F'-4 |
| Capacity of reactor [mL] | 230 | 230 | 1,000 | 1,000 |
| $SO_2F$ group-containing monomer | PSVE | PSVE | P2SVE | P2SVE |
| Amount of $SO_2F$ group-containing monomer [g] | 123.8 | 159.0 | 901.7 | 328.0 |
| HCFC-225cb [g] | 35.2 | 0.8 | 0 | 415.5 |
| Polymerization initiator | AIBN | IPP | IPP | V-601 |
| Amount of polymerization initiator [mg] | 63.6 | 47.9 | 90.7 | 223.7 |
| Polymerization temperature [° C.] | 70 | 40 | 40 | 70 |
| Polymerization pressure [MPaG] | 1.14 | 0.46 | 0.55 | 0.69 |
| Polymerization time [hr] | 7.9 | 13.6 | 7.0 | 3.7 |
| Yield of polymer F [g] | 25.1 | 28.1 | 64.8 | 104.1 |
| Ion exchange capacity [meq/g dry resin] | 1.10 | 1.44 | 1.87 | 1.46 |
| Units based on $SO_2F$ group-containing monomer [mol %] | 17.7 | 28.5 | 18.3 | 11.8 |
| Units based on $SO_2F$ group-containing monomer [mass %] | 49.0 | 64.0 | 58.4 | 45.6 |
| TQ value [° C.] | 225 | 238 | 296 | 241 |
| Tg [° C.] | 8 | 1 | −1 | 7 |

Ex. 4-5 to Ex. 4-7

The following polymers F'-5 to F'-7 were obtained in the same manner as in Ex. 4-1.

Polymer F'-5: units based on TFE/units based on P2SVE=80.6/19.4 (molar ratio), ion exchange capacity=1.93 meq/g dry resin.

Polymer F'-6: units based on TFE/units based on sPSVE=74.8/25.2 (molar ratio), ion exchange capacity=1.74 meq/g dry resin.

Polymer F'-7: units based on TFE/units based on sPSVE=83.9/16.1 (molar ratio), ion exchange capacity=1.25 meq/g dry resin.

Ex. 5

Ex. 5-1 to Ex. 5-4

Membranes of polymers H'-1 to H'-4 were obtained by treating the polymers F'-1 to F'-4 in the same manner as in Ex. 3. Results are shown in Table 4.

|  | Ex. 5-1 | Ex. 5-2 | Ex. 5-3 | Ex. 5-4 |
| --- | --- | --- | --- | --- |
| Used polymer F' | F'-1 | F'-2 | F'-3 | F'-4 |
| Obtained polymer H' | H'-1 | H'-2 | H'-3 | H'-4 |
| Used alkaline aqueous solution | Aqueous solution A | Aqueous solution C | Aqueous solution B | Aqueous solution C |
| Softening temperature [° C.] | 99 | 97 | 133 | 138 |
| Elastic modulus at 120° C. [MPa] | 2.70 | 1.81 | 12.5 | 40.8 |
| Conductivity [S/cm] | 0.050 | 0.089 | 0.151 | 0.102 |
| Moisture content [%] | 66 | 89 | 164 | 82 |

It is evident from Tables 1 to 4 that the compound 7-1 has a small molecular weight and has two $SO_2F$ groups, whereby even if the proportion of units based on the $SO_2F$ group-containing monomer in the polymer F obtained by copolymerization with TFE is made to be lower than that of the conventional polymer F', a polymer H having the ion exchange capacity at the same level can be obtained. The polymer F thereby has a high Tg, and the handling efficiency and the storage stability of the polymer F will improve. The polymer H has a high softening temperature for the same reason. Further, the polymer H has a low moisture content per ion exchange capacity, whereby a membrane of the polymer H which maintains the mechanical strength up to a high temperature can be formed. Further, the amount of expensive $SO_2F$ group-containing monomer to be used for the polymer F can be reduced as compared with the conventional polymer F', whereby the membrane of the polymer H can be produced at a low cost. On the other hand, in a case where the proportion of units based on the $SO_2F$ group-containing monomer in the polymer F is the same as the conventional polymer F', the ion exchange capacity of the polymer H can be increased, whereby a membrane of the polymer H which has a higher ion conductivity than the conventional polymer H', can be obtained.

Ex. 5-5 to Ex. 5-7

Membranes of polymers H'-5 to H'-7 were obtained by treating the polymers F'-5 to F'-7 in the same manner as in Ex. 3.

Ex. 6

Ex. 6-1

4.3 g of a membrane of the polymer H being cut into small pieces and 75 g of ultrapure water were added in a 100 mL container made of a polytetrafluoroethylene (PTFE), followed by heating at 200° C. for 24 hours. The contents were transferred to a tray made of PTFE and air-dried under nitrogen stream at 30° C. for 64 hours. 200 mL of the dried polymer H-1 was transferred in an autoclave made of glass, and 21.4 g of a mixed solvent of ultrapure water/ethanol (50/50 (mass ratio)) was added thereto. After stirring at 110° C. for 25 hours, 3.87 g of ultrapure water was added for dilution. After stirring at 90° C. for 5 hours, the reaction mixture was left to cool and subjected to filtration by means of a pressure filter (filter paper: PF040, manufactured by Advantec Toyo Kaisha, Ltd.) to obtain 31.9 g of liquid composition S-1 having 13.5 mass % of the polymer H-1 dispersed in the mixed solvent. The viscosity at 25° C. at a shear rate of 76.6 $s^{-1}$ was measured by means of an E-type viscometer, and it was 167 mPa·s.

Ex. 6-2

20.0 g of liquid composition S-3 having 10 mass % of the polymer H-3 dispersed in the mixed solvent was obtained in the same manner as in Ex. 6-1, except that 2.0 g of the polymer H-3, 9.0 g of ethanol and 9.0 g of water were used.

Ex. 6-3

6.5 g of the membrane of the polymer H-5 was immersed in a 10 mass % hydrogen peroxide solution and treated at 80° C. for 20 hours. After removing the hydrogen peroxide solution, the membrane of the polymer H-5 was immersed in a 3N hydrochloric acid aqueous solution at 80° C. for 30 minutes, and further immersed in ultrapure water at 80° C. for 15 minutes. A cycle of immersing in a hydrochloric acid aqueous solution and immersing in ultrapure water was carried out 5 times in total, and then, washing with ultrapure water was repeated until pH of ultrapure water in which the membrane of the polymer was immersed became 7.

6.5 g of the polymer H-5 treated with hydrogen peroxide and 48.4 g of a mixed solvent of ethanol/water (41/59 (mass ratio)) were added in a 200 mL autoclave made of glass, followed by heating with stirring. After stirring at 110° C. for 24 hours, 1.5 g of ethanol and 8.2 g of water were added. After stirring for 4 hours, the mixture was left to cool, followed by filtration by means of a pressure filter (filter paper: PF040, manufactured by Advantec Toyo Kaisha, Ltd.) to obtain 31.9 g of liquid composition S-5 having 10.9 mass % of the polymer H-5 dispersed in the mixed solvent. The viscosity was measured by means of an E-type viscometer at a shear rate of 76.6 $s^{-1}$ at 25° C., and it was 63.8 mPa·s.

Ex. 6-4

100 g of liquid composition S-4 having 2.1 mass % of the polymer H-4 dispersed in the mixed solvent was obtained in the same manner as in Ex. 6-1 except that 2.1 g the polymer H-4, 80.1 g of ethanol and 19.8 g of water were used.

Ex. 7

Ex. 7-1

20 g of a membrane of the polymer H'-1 being cut into small pieces and 56.9 g of a mixed solvent of ethanol/water (60/40 (mass ratio)) were added in an autoclave (internal capacity 200 mL, made of glass), and the autoclave was heated with stirring. After stirring at 115° C. for 16 hours, the autoclave was left to cool, followed by filtration by means of a pressure filter (filter paper: PF040, manufactured by Advantec Toyo Kaisha, Ltd.) to obtain 76.5 g of liquid composition S'-1 having 26.0 mass % of the polymer H'-1 dispersed in the mixed solvent. The viscosity at 25° C. at a shear rate of 76.6 s$^{-1}$ was measured by means of an E-type viscometer, and it was 357 mPa·s.

in Ex. 8-1, except that the liquid composition S'-1 was used, and the heat treatment was carried out at a temperature of 160° C. for 30 minutes. Results are shown in Table 5.

Ex. 9-2

A polymer electrolyte membrane made of the polymer H'-5 (thickness: 100 µm) was obtained in the same manner as in Ex. 9-1, except that the liquid composition S'-5 was used. Results are shown in Table 5.

Ex. 9-3

A polymer electrolyte membrane made of the polymer H'-6 (thickness: 100 µm) was obtained in the same manner as in Ex. 9-1, except that the liquid composition S'-6 was used. Results are shown in Table 5.

Ex. 9-4

A polymer electrolyte membrane made of the polymer H'-7 (thickness: 100 µm) was obtained in the same manner as in Ex. 9-1, except that the liquid composition S'-7 was used. Results are shown in Table 5.

TABLE 5

| Ex. | Ex. 8-1 | Ex. 8-2 | Ex. 8-3 | Ex. 9-1 | Ex. 9-2 | Ex. 9-3 | Ex. 9-4 |
|---|---|---|---|---|---|---|---|
| Polymer H/polymer H' | H-1 | H-3 | H-4 | H'-1 | H'-5 | H'-6 | H'-7 |
| Liquid composition used | S-1 | S-3 | S-4 | S'-1 | S'-5 | S'-6 | S'-7 |
| Softening temperature [° C.] | 151 | 145 | — | 99 | 137 | 121 | 130 |
| Conductivity [S/cm] | 0.132 | 0.197 | — | 0.050 | 0.171 | 0.128 | 0.071 |
| Moisture content [%] | 152 | At least 400 | — | 49 | 223 | 132 | 55 |
| Hydrogen gas permeability coefficient 1 [cm$^3$ · cm/(s · cm$^{-2}$ · cmHg)] | $2.1 \times 10^{-9}$ | — | $1.6 \times 10^{-9}$ | $5.5 \times 10^{-9}$ | $3.5 \times 10^{-9}$ | $3.3 \times 10^{-9}$ | $3.0 \times 10^{-9}$ |
| Hydrogen gas permeability coefficient 2 [cm$^3$ · cm/(s · cm$^{-2}$ · cmHg)] | $3.0 \times 10^{-9}$ | — | $2.3 \times 10^{-9}$ | $6.4 \times 10^{-9}$ | $4.2 \times 10^{-9}$ | $4.1 \times 10^{-9}$ | $3.6 \times 10^{-9}$ |

Ex. 7-2 to Ex. 7-4

Liquid compositions S'-5 to S'-7 were obtained from the membranes of the polymers H'-5 to H'-7 in the same manner as in Ex. 7-1.

Ex. 8

Ex. 8-1, Ex. 8-2 and Ex. 8-3

A polymer electrolyte membrane was obtained by using the liquid composition S-1, the liquid composition S-3 or the liquid composition S-4 by the following method.

A film was formed by applying the liquid composition on a 100 µm sheet made of an ethylene/tetrafluoroethylene copolymer by means of a die coater, followed by drying at 80° C. for 15 minutes and heat treatment at 185° C. for 30 minutes to obtain a polymer electrolyte membrane made of the polymer H (thickness: 25 µm). Results are shown in Table 5.

Ex. 9

Ex. 9-1

A polymer electrolyte membrane made of the polymer H'-1 (thickness: 25 µm) was obtained in the same manner as

Ex. 10

The liquid composition S-5 was applied on a sheet made of an ethylene/tetrafluoroethylene copolymer by a die coating method. Then, an oriented porous PTFE film (thickness: 20 µm, porosity: 80%) was immediately overlaid on the coating layer to impregnate the porous PTFE film with the liquid, followed by drying in an oven at 80° C. for 15 minutes and thermal treatment in the oven at 185° C. for 30 minutes to obtain an electrolyte membrane having a thickness of 50 µm.

Ex. 11

Ex. 11-1

Polymer F-6 (ion exchange capacity: 2.37 meq/g dry resin, TQ value: 158° C.) was obtained by copolymerizing TFE and the compound 7-1 in the same manner as in Ex. 2.

Further, polymer C-1 (ion exchange capacity: 1.06 meq/g dry resin, TQ value: 225° C.) was obtained by copolymerizing TFE and compound 11.

$$CF_2=CFOCF_2CF_2CF_2C(O)OCH_3 \qquad \text{Formula 11}$$

The polymer C-1 and the polymer F-6 were formed by a coextrusion method to obtain a film A of a two-layer structure consisting of a precursor layer (C') (thickness: 12 µm) made of the polymer C and an under layer (thickness: 68 µm) of a precursor layer S' made of the polymer F-6.

Further, the polymer F-6 was formed by a melt extrusion method to obtain a film B (thickness: 30 µm) to be an upper layer of the precursor layer S'.

A PTFE film was rapidly stretched and then slit into a width of 100 denier to obtain a monofilament, which was twisted 450 times/m to obtain a PTFE yarn, which was used as a reinforcing yarn. A PET yarn made of a multi-filament of 30 denier having six polyethylene terephthalate (PET) filaments of 5 denier aligned, was used as a sacrificial yarn. Plain weave was conducted so that one reinforcing yarn and two sacrificial yarns were alternately disposed, to obtain a reinforcing fabric (the density of reinforcing yarns: 27 yarns/inch, the density of sacrificial yarns: 54 yarns/inch).

The film B, the reinforcing fabric, the film A and a releasing PET film (thickness: 100 µm) were overlaid in this order so that the precursor layer C' of the film A was located on the releasing PET film side, and laminated by means of rolls. The releasing PET film was peeled off to obtain a reinforced precursor membrane.

A paste comprising 29.0 mass % of zirconium oxide (average particle diameter: 1 µm), 1.3 mass % of methyl cellulose, 4.6 mass % of cyclohexanol, 1.5 mass % of cyclohexane and 63.6 mass % of water, was transferred onto upper side of the precursor layer S' of the reinforced precursor membrane by a roll press, to form a gas-releasing coating layer. The attached amount of zirconium oxide was 20 g/m$^2$.

The reinforced precursor membrane having the gas-releasing coating layer formed on one side was immersed in a mixed aqueous solution of 5 mass % of dimethylsulfoxide and 30 mass % potassium hydroxide at 95° C. for 8 minutes. —C(O)OCH$_3$ in the polymer C-1 and —SO$_2$F in the polymer F-6 were thereby hydrolyzed and converted into ion exchange groups to obtain a membrane having a layer C formed from the precursor layer C' and a layer S formed from the precursor layer S'.

In an ethanol aqueous solution containing 2.5 mass % of a polymer obtained by hydrolyzing the polymer F'-1 into an acid form, zirconium oxide (average particle size: 1 µm) was dispersed at a concentration of 13 mass % to prepare a dispersion. The dispersion was sprayed on the layer C side of the membrane to form a gas-releasing coating layer to obtain a cation exchange membrane having gas-releasing coating layer s formed on both surfaces. The attached amount of zirconium oxide was 3 g/m$^2$.

Using an electrolytic bath having an effective current area of 1.5 dm$^2$ (height of 15 cm and width of 10 cm), a water inlet to a cathode chamber was disposed at a lower part of the cathode chamber, an outlet for sodium hydroxide aqueous solution to be produced was disposed at an upper part of the cathode chamber, a feed saline solution inlet to an anode chamber was disposed at a lower part of the anode chamber, and a brackish water outlet was disposed at an upper part of the anode chamber. As an anode, a punched metal (short diameter of 4 mm and long diameter of 8 mm) of titanium coated with a solid solution of ruthenium oxide, iridium oxide and titanium oxide was used. As a cathode, a punched metal (short diameter of 5 mm and long diameter of 10 mm) made of SUS304 electro-coated with Raney nickel containing ruthenium was used.

A cation exchange membrane was disposed so that the layer C would face the cathode in the electrolytic bath. The cathode side was pressurized so that the anode and the ion exchange membrane were in contact with each other, electrolysis was carried out for one week under conditions of a temperature of 90° C. and a current density of 8 kA/m$^2$ while supplying a 290 g/L sodium chloride aqueous solution and water to the anode chamber and the cathode chamber respectively, and maintaining the concentration of sodium chloride discharged from the anode chamber at 200 g/L and the concentration of sodium hydroxide discharged from the cathode chamber at 32 mass %, and cell voltage was read from terminals connected to the electrodes. Then, 0.1 ppm of magnesium was added to the sodium chloride aqueous solution as impurities, and electrolysis was carried out for 14 days. The difference in the voltage between 14th day after the addition and immediately before the addition was obtained. Results are shown in Table 6.

Ex. 11-2

Polymer F-7 (ion exchange capacity: 2.00 meq/g dry resin, TQ value: 238° C.) was obtained by copolymerizing TFE and the compound 7-1 in the same manner as in Ex. 2.

A cation exchange membrane was obtained in the same manner as in Ex. 11-1, except that the polymer F-7 was used instead of the polymer F-6. Results are shown in Table 6.

Ex. 11-3

Polymer F-8 (ion exchange capacity: 1.78 meq/g dry resin, TQ value: 298° C.) was obtained by copolymerizing TFE and the compound 7-1 in the same manner as in Ex. 2.

A cation exchange membrane was obtained in the same manner as in Ex. 11-1, except that the polymer F-8 was used instead of the polymer F-6. Results are shown in Table 6.

Ex. 11-4

Polymer F-9 (ion exchange capacity: 1.49 meq/g dry resin, TQ value: 268° C.) was obtained by copolymerizing TFE and the compound 7-1 in the same manner as in Ex. 2.

A cation exchange membrane was obtained in the same manner as in Ex. 11-1, except that the polymer F-9 was used instead of the polymer F-6. Results are shown in Table 6.

Ex. 12

Ex. 12-1

Polymer F'-8 (ion exchange capacity: 1.38 meq/g dry resin, TQ value: 230° C.) was obtained by copolymerizing TFE and compound 12 by a known method.

$$CF_2=CFCF_2OCF_2CF_2SO_2F \qquad \text{Formula 12}$$

A cation exchange membrane was obtained in the same manner as in Ex. 11-1, except that the polymer F'-8 was used instead of the polymer F-6. Results are shown in Table 6.

Ex. 12-2

Polymer F'-9 (ion exchange capacity: 1.19 meq/g dry resin, TQ value: 230° C.) was obtained by copolymerizing TFE and PSVE by a known method.

A cation exchange membrane was obtained in the same manner as in Ex. 11-1, except that the polymer F'-9 was used instead of the polymer F-6. Results are shown in Table 6.

Here, "units having a sulfonic acid group [mol %]" in Table 6 is the proportion (mol %) of units based on a monomer having a sulfonic acid group in all units constituting a polymer. Further, "proportion of functional groups

[mol %]" is an index representing the amount of sulfonic acid groups contained in a polymer molecule and is obtained by the following formula.

Proportion of functional groups [mol %]=units based on a monomer having a sulfonic acid group (mole)×the number of sulfonic acid groups in the monomer/all units (mole) based on all units contained in a polymer×100

For example, in the case of the compound 7-1, the monomer has two sulfonic acid groups, and the proportion of functional groups is a value obtained by multiplying the proportion of the monomer units having a sulfonic acid group by 2.

TABLE 6

| | Ex. 11-1 | Ex. 11-2 | Ex. 11-3 | Ex. 11-4 | Ex. 12-1 | Ex. 12-2 |
|---|---|---|---|---|---|---|
| Polymer F/polymer F' | F-6 | F-7 | F-8 | F-9 | F'-8 | F'-9 |
| Ion exchange capacity [meq/g dry resin] | 2.37 | 2.00 | 1.78 | 1.49 | 1.38 | 1.19 |
| Units having a sulfonic acid group [mol %] | 20.0 | 15.3 | 12.8 | 10.1 | 20.1 | 20.1 |
| Proportion of functional groups [mol %] | 40.0 | 30.5 | 25.6 | 20.1 | 20.1 | 20.1 |
| Initial current efficiency [%] | 97 | 97 | 97 | 97 | 97 | 97 |
| Initial electrolytic voltage [V] | 3.25 | 3.29 | 3.32 | 3.35 | 3.35 | 3.35 |
| Voltage rise due to magnesium addition [mV] | 31 | 40 | 51 | 60 | 72 | 73 |

By comparing Ex. 11-4, Ex. 12-1 and Ex. 12-2 wherein the proportion of functional group is the same, it is found that in Ex. 11-4 wherein the compound 7-1 was used as the starting material of a polymer, voltage rise due to magnesium can be more suppressed. Further, by comparing Ex. 11-1, Ex. 11-2, Ex. 11-3 and Ex. 11-4 wherein the compound 7-1 was used as a starting material of a polymer, it is found that the larger the ion exchange capacity, the smaller the value of voltage rise per magnesium, and the lower the initial electrolytic voltage.

INDUSTRIAL APPLICABILITY

The fluorosulfonyl group-containing polymer of the present invention is useful as a precursor for a polymer, etc. to be contained in a catalyst layer or a polymer electrolyte membrane for a membrane/electrode assembly for a polymer electrolyte fuel cell or in a catalyst layer or a polymer electrolyte membrane for a membrane/electrode assembly for polymer electrolyte type water electrolysis, a cation exchange membrane to be used for alkali chloride electrolysis or electrodialysis, an ion exchange membrane to be used for water electrolysis, a diaphragm for a redox flow secondary cell, an ion exchange membrane for an electrochemical hydrogen pump, etc.

REFERENCE SYMBOLS

10: membrane/electrode assembly, 11: catalyst layer, 12: gas diffusion layer, 13: anode, 14: cathode, 15: polymer electrolyte membrane, 16: carbon layer

What is claimed is:

1. A fluorosulfonyl group-containing polymer, comprising units represented by formula u1:

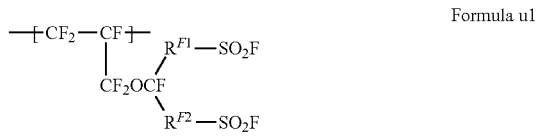

Formula u1 wherein $R^{F1}$ and $R^{F2}$ are a $C_{1-3}$ perfluoroalkylene group.

2. The fluorosulfonyl group-containing polymer according to claim 1, further comprising units based on tetrafluoroethylene.

3. The fluorosulfonyl group-containing polymer according to claim 1, which has a volume flow rate of from 200° C. to 330° C.

4. The fluorosulfonyl group-containing polymer according to claim 1, which has a glass transition temperature of from 5° C. to 70° C.

5. A sulfonic acid group-containing polymer, comprising units represented by formula u2:

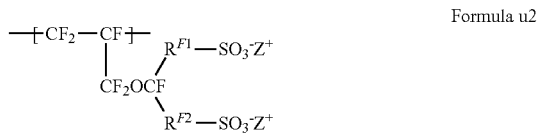

Formula u2 wherein $R^{F1}$ and $R^{F2}$ are a $C_{1-3}$ perfluoroalkylene group, and $Z^+$ is $H^+$, a metal ion or an ammonium ion.

6. The sulfonic acid group-containing polymer according to claim 5, further comprising units based on tetrafluoroethylene.

7. The sulfonic acid group-containing polymer according to claim 5, which has an ion exchange capacity of from 0.5 meq/g dry resin to 2.5 meq/g dry resin.

8. The sulfonic acid group-containing polymer according to claim 5, which has a softening temperature of from 100° C. to 180° C.

9. The sulfonic acid group-containing polymer according to claim 5, which has a moisture content of from 30 mass % to 300 mass %.

10. A method for producing a sulfonic acid group-containing polymer, the method comprising
   hydrolyzing fluorosulfonyl groups in the fluorosulfonyl group-containing polymer according to claim 1 into salt form sulfonic acid groups, and
   optionally converting the salt form sulfonic acid groups into acid form sulfonic acid groups.

11. The method according to claim 10, further comprising treating the sulfonic acid group-containing polymer obtained after said hydrolyzing or said converting with a hydrogen peroxide solution.

12. A liquid composition, comprising
   the sulfonic acid group-containing polymer according to claim 5 and
   a liquid medium.

13. A membrane, comprising the sulfonic acid group-containing polymer according to claim 5.

14. The membrane according to claim 13, further comprising a reinforcing material.

15. A method for producing a membrane, the method comprising
   applying the liquid composition according to claim 12 on a substrate, followed by drying.

16. A method for producing a membrane, the method comprising
   extruding the fluorosulfonyl group-containing polymer according to claim 1 into a membrane form, and
   converting the fluorosulfonyl groups into sulfonic acid groups.

17. A method for producing a membrane, the method comprising
   impregnating a reinforcing material with the liquid composition according to claim 12, followed by drying.

18. A polymer electrolyte membrane, comprising the sulfonic acid group-containing polymer according to claim 5.

19. A catalyst layer, comprising sulfonic acid group-containing polymer according to claim 5 and a catalyst.

20. A membrane/electrode assembly, comprising a catalyst layer of a cathode, a catalyst layer of an anode, and a polymer electrolyte membrane, wherein at least one selected from the group consisting of the catalyst layer of a cathode, the catalyst layer of an anode, and the polymer electrolyte membrane comprises the sulfonic acid group-containing polymer according to claim 5.

21. A polymer electrolyte fuel cell, comprising the membrane/electrode assembly according to claim 20.

22. A cation exchange membrane for alkali chloride electrolysis, comprising the sulfonic acid group-containing polymer according to claim 5.

23. An ion exchange membrane for water electrolysis, comprising the sulfonic acid group-containing polymer according to claim 5.

24. A diaphragm for a redox flow secondary cell, comprising the sulfonic acid group-containing polymer according to claim 5.

25. An ion exchange membrane for an electrochemical hydrogen pump, comprising the sulfonic acid group-containing polymer according to claim 5.

26. An acid form sulfonic acid group-containing fluorocarbon polymer, which has a hydrogen gas permeability coefficient of at most $2.9 \times 10^{-9}$ cm$^3$·cm/(s·cm$^2$·cmHg) under conditions of a temperature of 80° C. and a relative humidity of 10%.

27. The acid form sulfonic acid group-containing fluorocarbon polymer according to claim 26, which has an ion exchange capacity of at least 0.9 meq/g dry resin.

28. A polymer electrolyte membrane, comprising the acid form sulfonic acid group-containing fluorocarbon polymer according to claim 26.

29. The polymer electrolyte membrane according to claim 28, which has a thickness of from 5 μm to 200 μm.

\* \* \* \* \*